United States Patent
Iwasaka et al.

(10) Patent No.: US 10,595,709 B2
(45) Date of Patent: Mar. 24, 2020

(54) ENDOSCOPIC SURGERY DEVICE

(71) Applicant: FUJIFILM Corporation, Tokyo (JP)

(72) Inventors: Masayuki Iwasaka, Kanagawa (JP); Takumi Dejima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 277 days.

(21) Appl. No.: 14/868,395

(22) Filed: Sep. 29, 2015

(65) Prior Publication Data

US 2016/0015254 A1 Jan. 21, 2016

Related U.S. Application Data

(63) Continuation of application No. PCT/JP2014/058780, filed on Mar. 27, 2014.

(30) Foreign Application Priority Data

Mar. 29, 2013 (JP) ................................. 2013-074016

(51) Int. Cl.
*A61B 1/00* (2006.01)
*A61B 1/313* (2006.01)
(Continued)

(52) U.S. Cl.
CPC ...... *A61B 1/00087* (2013.01); *A61B 1/00006* (2013.01); *A61B 1/0016* (2013.01);
(Continued)

(58) Field of Classification Search
CPC ............ A61B 1/00087; A61B 1/00135; A61B 1/00154; A61B 1/0016; A61B 1/045;
(Continued)

(56) References Cited

U.S. PATENT DOCUMENTS 4,618,885 A * 10/1986 Nagasaki ................. A61B 1/05
128/901
4,930,494 A * 6/1990 Takehana ........... A61B 1/00147
600/145
(Continued)

FOREIGN PATENT DOCUMENTS

JP 09-028663 2/1997
JP 09-266882 10/1997
(Continued)

OTHER PUBLICATIONS

"Office Action of China Counterpart Application" with machine English translation, dated Jul. 18, 2016, p. 1-p. 15.
(Continued)

*Primary Examiner* — Timothy J Neal
*Assistant Examiner* — Jae Woo
(74) *Attorney, Agent, or Firm* — JCIPRNET

(57) ABSTRACT

The endoscopic surgery device includes: an outer tube body that penetrates through a body wall to be inserted into a body cavity; an endoscope insertion path provided inside the outer tube body; a treatment tool insertion path provided inside the outer tube body; a position sensor that has a non-sensitive area where no change in a relative position of the treatment tool insertion part with respect to the endoscope insertion part is detected even if the treatment tool insertion part is moved back and forth, and a sensitive area that is an area other than the non-sensitive area, where change in a relative position of the treatment tool insertion part is detected, and that detects its movement amount with respect to the outer tube body; and a control unit that changes a range of an observation image acquired by the endoscope in accordance with the detected movement amount.

12 Claims, 15 Drawing Sheets

(51) Int. Cl.
*A61B 1/045* (2006.01)
*A61B 1/05* (2006.01)
*A61B 17/34* (2006.01)
*A61B 1/06* (2006.01)
*A61B 90/00* (2016.01)

(52) U.S. Cl.
CPC ...... *A61B 1/00135* (2013.01); *A61B 1/00154* (2013.01); *A61B 1/045* (2013.01); *A61B 1/05* (2013.01); *A61B 1/0676* (2013.01); *A61B 1/3132* (2013.01); *A61B 17/3421* (2013.01); *A61B 17/3462* (2013.01); *A61B 2017/3409* (2013.01); *A61B 2017/3441* (2013.01); *A61B 2017/3445* (2013.01); *A61B 2017/3447* (2013.01); *A61B 2017/3466* (2013.01); *A61B 2090/0811* (2016.02)

(58) Field of Classification Search
CPC ....... A61B 1/05; A61B 1/0676; A61B 1/3132; A61B 17/3421; A61B 2090/0811; A61B 2017/3441; A61B 2017/3445; A61B 2017/3466; A61B 34/75; A61B 34/77
USPC .................................................. 600/117, 114
See application file for complete search history.

(56) References Cited

U.S. PATENT DOCUMENTS

| | | | | |
|---|---|---|---|---|
| 5,382,885 A * | 1/1995 | Salcudean | ................. | B25J 3/04 318/568.1 |
| 5,558,619 A * | 9/1996 | Kami | ................. | A61B 1/00006 600/106 |
| 5,762,458 A * | 6/1998 | Wang | ................. | B25J 9/1689 414/1 |
| 5,836,869 A | 11/1998 | Kudo et al. | | |
| 5,855,583 A * | 1/1999 | Wang | ................. | B25J 9/1689 318/568.11 |
| 6,063,095 A * | 5/2000 | Wang | ................. | A61B 34/75 128/898 |
| 6,096,004 A * | 8/2000 | Meglan | ................. | A61B 34/75 604/95.01 |
| 6,221,007 B1 * | 4/2001 | Green | ................. | A61B 1/00052 600/104 |
| 6,238,384 B1 * | 5/2001 | Peer | ................. | A61B 17/062 128/898 |
| 6,245,028 B1 * | 6/2001 | Furst | ................. | A61B 10/0233 600/411 |
| 6,699,177 B1 * | 3/2004 | Wang | ................. | A61B 34/75 414/2 |
| 6,962,563 B2 * | 11/2005 | Yasunaga | ................. | A61B 1/00149 600/114 |
| 8,105,230 B2 * | 1/2012 | Honda | ................. | A61B 1/00059 600/104 |
| 9,131,957 B2 * | 9/2015 | Skarbnik | ................. | A61B 17/3421 |
| 2004/0024311 A1 * | 2/2004 | Quaid, III | ................. | A61B 34/20 600/428 |
| 2004/0106916 A1 * | 6/2004 | Quaid | ................. | A61B 34/20 606/1 |
| 2005/0119525 A1 * | 6/2005 | Takemoto | .......... | A61B 1/00154 600/114 |
| 2007/0142823 A1 * | 6/2007 | Prisco | ................. | B25J 9/1638 606/1 |
| 2007/0232863 A1 * | 10/2007 | Miyake | ................. | A61B 1/00045 600/204 |
| 2007/0265502 A1 * | 11/2007 | Minosawa | ......... | A61B 1/00177 600/173 |
| 2008/0188868 A1 * | 8/2008 | Weitzner | ................. | A61B 1/0014 606/130 |
| 2009/0234223 A1 * | 9/2009 | Onoda | ................. | A61B 5/06 600/424 |
| 2009/0275798 A1 * | 11/2009 | Naito | ................. | A61B 1/00149 600/106 |
| 2010/0016666 A1 * | 1/2010 | Hasegawa | ............ | A61B 1/018 600/118 |
| 2010/0114288 A1 * | 5/2010 | Haller | ................. | A61B 17/3468 607/137 |
| 2011/0178508 A1 * | 7/2011 | Ullrich | ............ | A61B 17/00234 606/1 |
| 2011/0202068 A1 * | 8/2011 | Diolaiti | .................... | B25J 9/161 606/130 |
| 2011/0245661 A1 * | 10/2011 | Yoshie | ..................... | A61B 1/04 600/424 |
| 2011/0295268 A1 * | 12/2011 | Roelle | .................... | B25J 9/1689 606/130 |
| 2012/0059391 A1 * | 3/2012 | Diolaiti | .................. | B25J 9/1689 606/130 |
| 2013/0123759 A1 * | 5/2013 | Kang | ..................... | A61B 34/72 606/1 |
| 2014/0135794 A1 * | 5/2014 | Cau | ........................ | A61B 34/37 606/130 |
| 2014/0135795 A1 * | 5/2014 | Yanagihara | ............ | A61B 34/77 606/130 |
| 2014/0303660 A1 * | 10/2014 | Boyden | .................. | A61B 17/32 606/170 |
| 2015/0080650 A1 * | 3/2015 | Dejima | .............. | A61B 1/00135 600/102 |
| 2015/0196228 A1 * | 7/2015 | Akimoto | .................. | A61B 1/05 600/109 |
| 2016/0015245 A1 * | 1/2016 | Iwasaka | ............. | A61B 17/3421 600/106 |
| 2016/0015255 A1 * | 1/2016 | Dejima | .............. | A61B 1/00135 600/106 |
| 2016/0015256 A1 * | 1/2016 | Iwasaka | ............. | A61B 17/3421 600/106 |
| 2016/0022118 A1 * | 1/2016 | Dejima | .............. | A61B 1/00154 600/104 |
| 2016/0022122 A1 * | 1/2016 | Dejima | .............. | A61B 1/00087 600/210 |
| 2016/0128547 A1 * | 5/2016 | Ogawa | ............... | A61B 1/00133 600/107 |
| 2016/0174825 A1 * | 6/2016 | Dejima | .............. | A61B 1/00135 600/104 |
| 2016/0175004 A1 * | 6/2016 | Dejima | .............. | A61B 1/00135 600/114 |
| 2016/0175005 A1 * | 6/2016 | Dejima | .............. | A61B 1/00135 600/114 |
| 2016/0175006 A1 * | 6/2016 | Dejima | .............. | A61B 1/00112 600/114 |
| 2016/0183772 A1 * | 6/2016 | Hatta | ................. | A61B 1/00087 600/106 |
| 2016/0302653 A1 * | 10/2016 | Inoue | ....................... | G01C 3/08 |
| 2016/0331208 A1 * | 11/2016 | Kikuchi | ................. | A61B 90/57 |

FOREIGN PATENT DOCUMENTS

| | | |
|---|---|---|
| JP | 10-179512 | 7/1998 |
| JP | 2002-017752 | 1/2002 |
| JP | 2002-209835 | 7/2002 |
| JP | 2004041778 A * | 2/2004 |
| JP | 2004-141486 | 5/2004 |
| JP | 2004-180858 | 7/2004 |
| JP | 2005-095634 | 4/2005 |
| JP | 2007/222239 | 9/2007 |
| JP | 2007-301378 | 11/2007 |
| JP | 2008132352 A * | 6/2008 |
| WO | 2013/176167 | 11/2013 |

OTHER PUBLICATIONS

"Search Report of European Counterpart Application", dated May 19, 2016, p. 1-p. 7.

"Written Opinion of the International Searching Authority" of PCT/JP2014/058780, dated May 13, 2014, with English translation thereof, pp. 1-10, in which five of the listed references (JP2005-095634, JP2007-301378, JP10-179512, JP2007-222239 and JP09-266882) were cited.

(56) References Cited

OTHER PUBLICATIONS

"Office Action of Japan Counterpart Application" with English translation thereof, dated Aug. 30, 2016, p. 1-p. 6.

* cited by examiner (A)

(B)

ENDOSCOPIC SURGERY DEVICE

CROSS-REFERENCE TO RELATED APPLICATIONS

This application is a Continuation of PCT International Application No. PCT/JP2014/058780 filed on Mar. 27, 2014, which claims priority under 35 U.S.C. § 119(a) to Japanese Patent Application No. 2013-074016 filed on Mar. 29, 2013. Each of the above application(s) is hereby expressly incorporated by reference, in its entirety, into the present application.

BACKGROUND OF THE INVENTION

Field of the Invention

The present invention relates to an endoscopic surgery device, and particularly relates to an endoscopic surgery device that can operate an endoscope and a treatment tool which are inserted in a body cavity in interlock with each other.

Description of the Related Art

Recently, endoscopic surgery using an endoscope (rigid endoscope) such as a laparoscope is widely performed because invasion to a patient is small as compared with surgery in which laparotomy and thoracotomy, and so on, are performed. For example, in laparoscopic surgery, a trocar is inserted in multiple places of patient's abdomen, an endoscope, a treatment tool or the like is inserted in a body cavity using an insertion hole formed in the trocar as a guide, and various kinds of treatments are performed using the treatment tool while observing an observation image (endoscope image) by a monitor.

In general, a surgeon's hands are busy by the operation of treatment tools in endoscopic surgery. Therefore, the operation of an endoscope is performed by an assistant who is called a scopist. However, in a case where the assistant operates the endoscope, the surgeon has to sequentially give an instruction to the assistant, and there are problems that a work to correctly turn the direction of the endoscope to a direction desired by the surgeon is difficult and the surgeon suffers stress. Moreover, since the assistance performs an operation after the surgeon gives an instruction, there is a problem of taking time to perform a surgery. In addition, the assistant has to operate the endoscope so as not to obstruct the surgeon's surgery, and there is a problem that the operation is likely to become complicated.

Meanwhile, Japanese Patent Application Laid-Open No. 2007-301378 (PTL 1) discloses a technique that inserts a treatment tool and an endoscope from opening portions formed in different positions in a body wall into body cavities respectively in endoscopic surgery and synchronously moves the endoscope according to the movement of the treatment tool. According to this technique, since the endoscope synchronously moves according to the surgeon's operation of the treatment tool, the assistant's operation of the endoscope becomes unnecessary, the surgeon's stress with the assistant is eliminated, the surgeon can perform a surgery as desired, and therefore it is convenient. Moreover, in the technique disclosed in PTL 1, to prevent an observation image obtained by the endoscope from minutely moving and being difficult to be seen, it is determined whether the distal end of the treatment tool is in the inner region of the observation image or it is in a peripheral region, the visual field of the endoscope is not changed in a case where the distal end of the treatment tool exists in the inner region of the observation image, and the visual field of the endoscope is changed such that the distal end of the treatment tool comes to the center of the observation image in a case where the distal end of the treatment tool exists in the outer region. By this means, it becomes possible to prevent the image from being rather difficult to be seen due to the minute movement of the observation image in interlock with the minute movement of the treatment tool.

Moreover, Japanese Patent Application Laid-Open No. 2004-180858 (PTL 2) and Japanese Patent Application Laid-Open No. 2004-141486 (PTL 3) disclose a technique in which: two insertion holes are provided in an outer tube which penetrates through a body wall and is inserted in a body cavity; and the endoscope is inserted in one insertion hole and the treatment tool is inserted in the other insertion hole. According to this technique, low invasion is achieved because it is possible to reduce the number of opening portions formed in a body wall to insert the treatment tool and the endoscope in the body cavity.

SUMMARY OF THE INVENTION

However, in the technique disclosed in PTL 1, it is effective in a case where the distal end of the treatment tool moves in a direction orthogonal to the visual field direction of the endoscope, but, if a zoom device is moved in interlock with a back-and-forth movement in the axial direction of the treatment tool, the size of an observation target changes in interlock with the minute movement of the treatment tool, and there is a problem that a depth perception is difficult to be recognized.

Moreover, in PTL 2 and PTL 3, there is no technical idea of synchronously moving the endoscope and the treatment tool which are inserted in the same outer tube, and there is no description that suggests a problem caused when the endoscope and the treatment tool are moved in interlock with each other.

The present invention is made in view of such circumstances, and aims to provide an endoscopic surgery device with high operability that can easily obtain an image desired by a surgeon.

In order to achieve the object described above, an endoscopic surgery device according to the present invention includes: a guide member configured to penetrate through a body wall to be inserted into a body cavity; an endoscope insertion path which is provided inside the guide member, and into which an endoscope configured to observe an inside of the body cavity is insertable in a back-and-forth movable manner; a treatment tool insertion path which is provided inside the guide member, and into which a treatment tool configured to inspect or treat a diseased part in the body cavity is insertable in a back-and-forth movable manner; detection means (detection unit) including a non-sensitive area where no change in a relative position of the treatment tool with respect to the endoscope is detected even if the treatment tool inserted into the treatment tool insertion path is moved back and forth, and a sensitive area which is an area other than the non-sensitive area, in which change in a relative position of the treatment tool is detected when the treatment tool is moved back and forth, the detection means configured to detect a movement amount of the treatment tool with respect to the guide member in the sensitive area; and control means (control unit) configured to change a range of an observation image acquired by the endoscope in accordance with the movement amount of the treatment tool detected by the detection means.

One aspect of the endoscopic surgery device according to the present invention includes an interlocking member configured to be movable inside the treatment tool insertion path in interlock with the back-and-forth movement of the treatment tool, the interlocking member being provided with an allowance part (play part) corresponding to the non-sensitive area, beyond which the interlocking member starts moving in interlock with the back-and-forth movement of the treatment tool, wherein the detection means detects the movement amount of the treatment tool by detecting a movement amount of the interlocking member.

In addition, in another aspect of the endoscopic surgery device according to the present invention, the treatment tool is provided, on an outer circumference part thereof, with a scale area corresponding to the sensitive area which is periodically arranged along an axial direction of the treatment tool, and a non-scale area corresponding to the non-sensitive area that is arranged other than the scale area, and when the treatment tool moves back and forth, the detection means detects the movement amount of the treatment tool by optically, magnetically, or electronically reading the scale area, and does not detect the movement amount of the treatment tool in the non-scale area.

Further, in yet another aspect of the endoscopic surgery device according to the present invention, the detection means includes calculation means (calculation unit) configured to calculate the movement amount of the treatment tool in the observation image; first conversion means (first conversion unit) configured to convert the movement amount of the treatment tool in the observation image calculated by the calculation means into an actual movement amount; and second conversion means (second conversion unit) configured to set the actual movement amount of the treatment tool to zero when the actual movement amount of the treatment tool is less than a predetermined range.

Furthermore, in yet another aspect of the endoscopic surgery device according to the present invention, the control means changes the range of the observation image acquired by the endoscope in proportion to the movement amount of the treatment tool.

In addition, in yet another aspect of the endoscopic surgery device according to the present invention, the control means is endoscope movement control means (endoscope movement control unit) configured to move back and forth the endoscope inserted into the endoscope insertion path based on a detection result of the detection means.

Further, in yet another aspect of the endoscopic surgery device according to the present invention, the control means is zoom control means (zoom control unit) configured to change magnification of the observation image acquired by the endoscope based on a detection result of the detection means.

Furthermore, in yet another aspect of the endoscopic surgery device according to the present invention, the endoscope includes a zoom lens configured to be movable in an optical axis direction, and the zoom control means includes optical zoom control means (optical zoom control unit) configured to change the magnification of the observation image by moving the zoom lens in the optical axis direction based on the detection result by the detection means.

In addition, in yet another aspect of the endoscopic surgery device according to the present invention, the zoom control means includes electronic zoom control means (electronic zoom control unit) configured to change the magnification of the observation image acquired by the endoscope by performing electronic variable magnification processing to the observation image based on the detection result by the detection means.

According to the present invention, a range of an observation image acquired by an endoscope is changed with an allowance with respect to a back-and-forth movement of a treatment tool. Accordingly, it is possible to prevent a size of an observation target from changing in a case where an insertion part of the treatment tool is slightly displaced in an axial direction (in a case of a back-and-forth movement of a small amplitude is performed). As a result, a depth perception can be properly kept to enable a stable observation image to be provided. In addition, in a case where the treatment tool is largely displaced in the axial direction (in a case of a back-and-forth movement of a large amplitude is performed), since a range of an observation image acquired by the endoscope is changed in interlock with the displacement, a size of the observation target changes in response to operation of the treatment tool. As a result, it is possible to easily acquire an image desired by a surgeon to allow operability to be improved.

DETAILED DESCRIPTION OF THE EMBODIMENTS

Hereinafter, referring to accompanying drawings, a preferable embodiment of the present invention will be described in detail. Every drawing shows a main part that is emphasized for explanation, and is sometimes shown by a different dimension from an actual dimension.

First Embodiment

Figure 1:
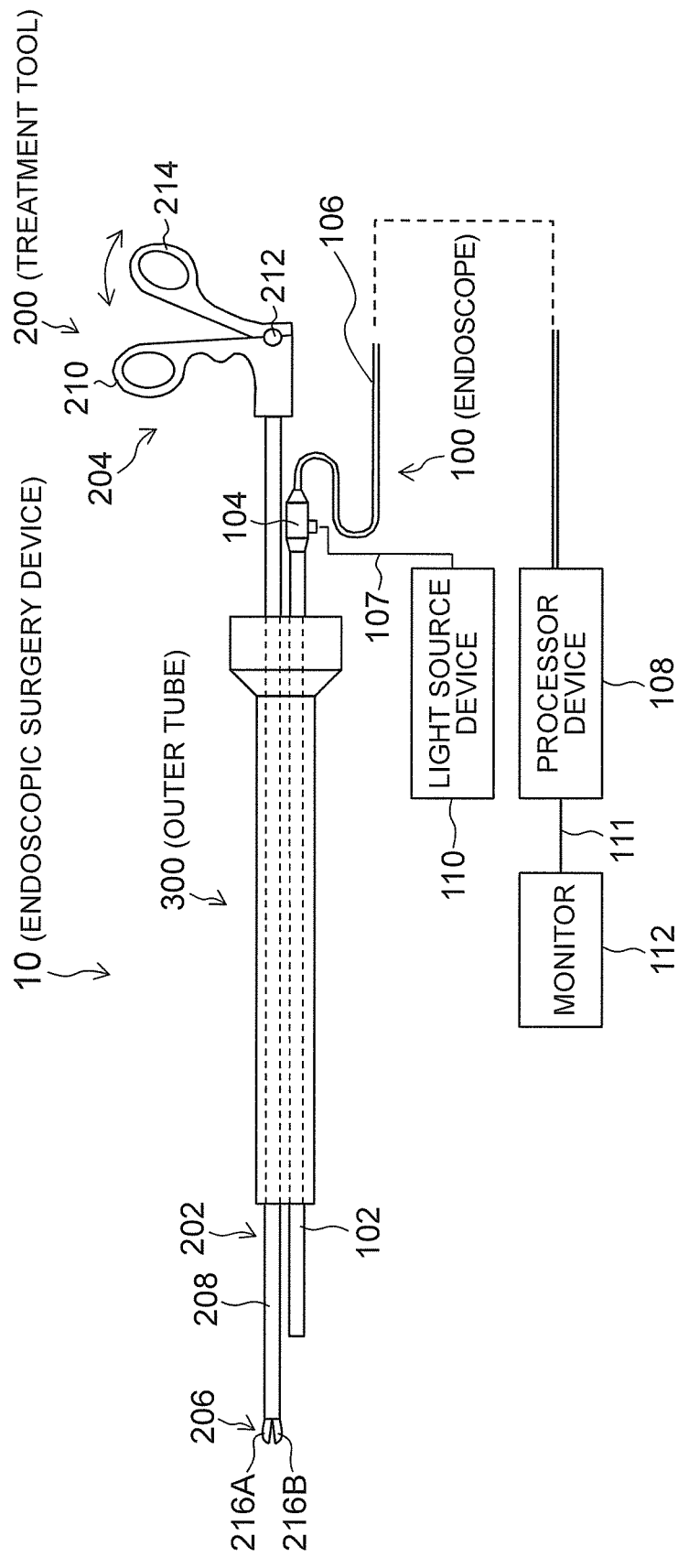
FIG. 1 is a schematic configuration diagram showing an endoscopic surgery device according to a first embodiment.

FIG. 1 is a schematic configuration diagram showing an endoscopic surgery device according to the first embodiment. As shown in FIG. 1, an endoscopic surgery device 10 of the present embodiment includes an endoscope 100 that observes the inside of a body cavity of a patient, a treatment tool 200 for inspecting or treating a diseased part in the body cavity of the patient, and an outer tube 300 that guides the endoscope 100 and the treatment tool 200 into the body cavity.

The endoscope 100 is a rigid endoscope such as a laparoscope, for example, and includes an elongated insertion part (hereinafter referred to as an "endoscope insertion part") 102 to be inserted into a body cavity, and an operation part 104 connected to a proximal end side of the endoscope insertion part 102. A universal cable 106 is connected to the operation part 104, and a processor device 108 is detachably connected to a top end of the universal cable 106 through a connector (not shown). In addition, the processor device 108 is connected to a monitor 112 through a cable 111. Further, a light cable 107 extends from a side portion of the operation part 104, and a connector (not shown) is provided at a top end of the light cable 107. The connector is detachably connected to a light source device 110.

Figure 2:
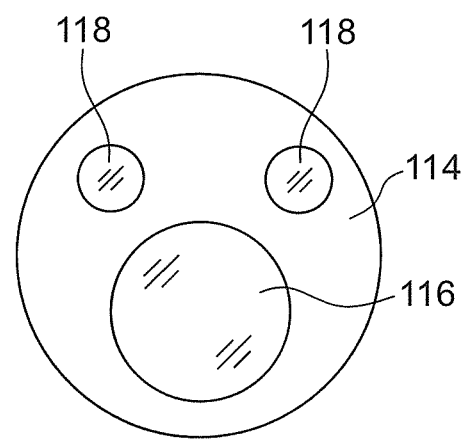
FIG. 2 is a plan view showing a distal end surface of an insertion part of an endoscope.

As shown in FIG. 2, an observation window 116 and illumination windows 118 and 118 are provided in a distal end surface 114 of the endoscope insertion part 102.

Behind the observation window 116, there are arranged an objective lens of an observation optical system, and an imaging element arranged at an imaging position of the objective lens, such as a charge coupled device (CCD) and a complementary metal-oxide semiconductor (CMOS). A signal cable (not shown) is connected to a substrate supporting the imaging element. The signal cable is inserted into the endoscope insertion part 102, the operation part 104, the universal cable 106, and the like, shown in FIG. 1, to extend to a connector (not shown), and then connected to the processor device 108. An observation image captured through the observation window 116 is imaged in a receiving surface of the imaging element to be converted into an electric signal (an imaging signal), and then the electric signal is outputted to the processor device 108 through the signal cable to be converted into a video signal. Then, the video signal is outputted to the monitor 112 connected to the processor device 108 so that the observation image (endoscope image) is displayed in a screen of the monitor 112.

Behind the illumination windows 118 and 118 of FIG. 2, an emission end of a light guide (not shown) is arranged. The light guide is inserted into the endoscope insertion part 102, the operation part 104, and the light cable 107, shown in FIG. 1, and an incident end thereof is arranged in a connector (not shown). Thus, the connector is coupled to the light source device 110, so that illumination light emitted from the light source device 110 is transmitted to the illumination windows 118 and 118 through the light guide to be emitted forward through the illumination windows 118 and 118. In FIG. 2, although the two illumination windows 118 and 118 are provided in the distal end surface 114 of the endoscope insertion part 102, the number of the illumination windows 118 is not limited, and the number may be one, or three or more.

As shown in FIG. 1, the treatment tool 200 is composed of forceps, for example, and includes an elongated insertion part (hereinafter referred to as a "treatment tool insertion part") 202 to be inserted into a body cavity, an operation part 204 that is provided on a proximal end side of the treatment tool insertion part 202 to be held by a surgeon, and a treatment part 206 that is provided on a distal end side of the treatment tool insertion part 202 to be movable by operation of the operation part 204.

The treatment tool insertion part 202 is provided with a cylindrical sheath 208 and an operation shaft (not shown) that is movably inserted into the sheath 208 in an axis direction. In addition, the operation part 204 is provided with a fixed handle 210 and a movable handle 214 that is rotatably coupled to the fixed handle 210 through a rotation pin 212. Further, a proximal end of the operation shaft is coupled to the movable handle 214.

The treatment part 206 is provided with a pair of holding members 216A and 216B that can be opened and closed. The holding members 216A and 216B are coupled to a distal end of the operation shaft through a drive mechanism (not shown). Then, the holding members 216A and 216B of the treatment part 206 are opened or closed through the operation shaft and the drive mechanism, according to rotation operation of the movable handle 214 of the operation part 204.

The treatment tool 200 is not limited to forceps, and another treatment tool, such as a laser probe, a suture instrument, an electric knife, a needle holder, and an ultrasound aspirator, for example, may be used.

Figure 3:
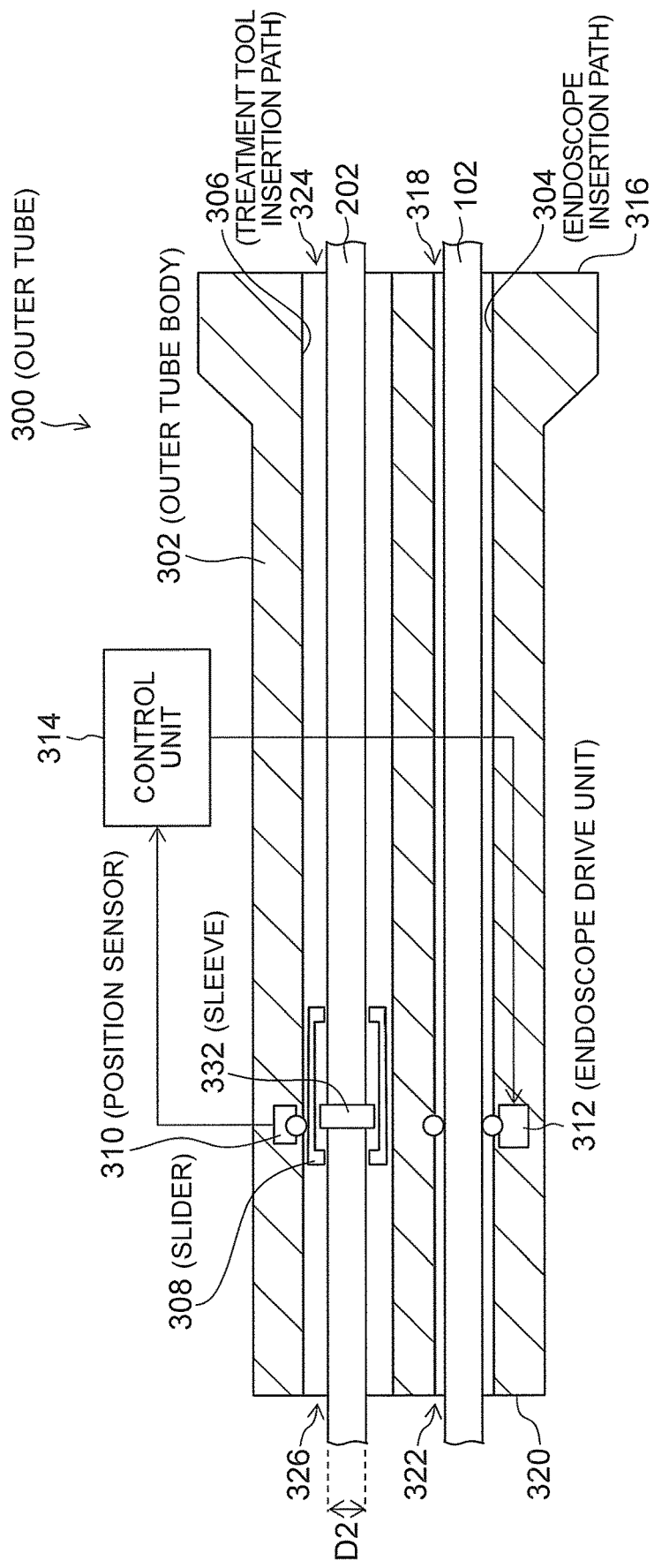
FIG. 3 is a schematic diagram showing an internal structure of an outer tube.
Figure 4:
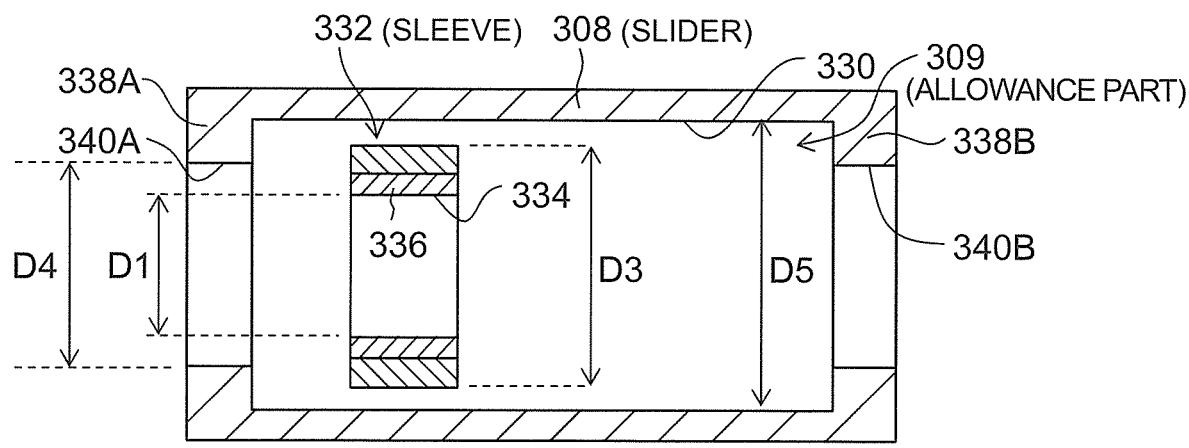
FIG. 4 is a configuration diagram showing a structure of a slider and a sleeve that are components of an outer tube.

FIG. 3 is a schematic diagram showing an internal structure of the outer tube 300. FIG. 4 is a configuration diagram showing a structure of a slider 308 and a sleeve 332 that are components of the outer tube 300.

As shown in FIG. 3, the outer tube 300 includes an outer tube body 302, an endoscope insertion path 304, a treatment tool insertion path 306, a slider 308, a position sensor 310, an endoscope drive unit 312, and a control unit 314.

The outer tube body 302 is a guide member that penetrates through a body wall of a patient to be inserted into a body cavity. The endoscope insertion path 304 and the treatment tool insertion path 306 are provided inside the outer tube body 302.

The endoscope insertion path 304 is formed so as to penetrate through the outer tube body 302 along the axial direction of the outer the body 302, and is configured as an insertion path in which the endoscope insertion part 102 can be inserted (insertable) in a back-and-forth movable manner. The endoscope insertion path 304 communicates with an endoscope entry port 318 opened to a proximal end face 316 of the outer tube body 302 and communicates with an endoscope exit port 322 opened to a distal end surface 320 of the outer tube body 302. Accordingly, a distal end of the endoscope insertion part 102 inserted into the endoscope entry port 318 is delivered out from the endoscope exit port 322 through the endoscope insertion path 304.

The treatment tool insertion path 306 is formed so as to penetrate through the outer tube body 302 along the axial direction of the outer tube body 302, and is configured so that the treatment tool insertion part 202 can be inserted in the treatment tool insertion path 306 in a back-and-forth movable manner. The treatment tool insertion path 306 communicates with a treatment tool entry port 324 opened to the proximal end face 316 of the outer tube body 302 and communicates with a treatment tool exit port 326 opened to the distal end surface 320 of the outer tube body 302. Accordingly, the treatment part 206 that is a distal end of the treatment tool insertion part 202, inserted into the treatment tool entry port 324, is delivered out from the treatment tool exit port 326 through the treatment tool insertion path 306.

Each of the endoscope insertion path 304 and the treatment tool insertion path 306 is provided with a check valve and a seal member, which are not shown, to secure air tightness in a body cavity. Accordingly, it is possible to prevent carbon dioxide gas injected into the body cavity from flowing out from the body cavity through the endoscope insertion path 304 and the treatment tool insertion path 306. In addition, a stopper portion (not shown) for preventing the slider 308 described later from falling out is provided in an end part of each of the distal end side and the proximal end side of the treatment tool insertion path 306.

The slider 308 is an interlocking member that is movable in the treatment tool insertion path 306 in interlock with the back-and-forth movement of the treatment tool insertion part 202, with an allowance with respect to the movement of the treatment tool insertion part 202. The slider 308 is formed in a cylindrical shape, and a guide hole 330 constituting an allowance part 309 is provided inside the slider 308. The guide hole 330 is formed along the axial direction, and a sleeve 332 is accommodated inside the guide hole 330. As shown in FIG. 4, an outer diameter D3 of the sleeve 332 is formed to be smaller than an inner diameter D5 of the guide hole 330. Accordingly, the sleeve 332 is configured to be movable along an axial direction of the guide hole 330.

A treatment tool holding hole 334 which is formed so as to penetrate through the sleeve 332 along the axial direction is provided inside the sleeve 332. An inner wall part of the treatment tool holding hole 334 is formed with a cylindrical elastic member 336. An inner diameter D1 of the treatment tool holding hole 334 is formed to be slightly smaller than an outer diameter (an outer diameter of a part held by the treatment tool holding hole 334) D2 of the treatment tool insertion part 202 (see FIG. 3). Therefore, by inserting the treatment tool insertion part 202 into the treatment tool holding hole 334, the sleeve 332 is held in a state where the sleeve 332 is brought into close contact with an outer peripheral surface of the treatment tool insertion part 202 by elastic force of the elastic member 336. Accordingly, the sleeve 332 becomes movable integrally with the treatment tool insertion part 202. Here, since holding is achieved by elastic force of the elastic member 336, a holding position of the treatment tool insertion part 202 can be arbitrarily adjusted with respect to the sleeve 332.

The slider 308 is provided at its both ends in the axial direction with stopper portions 338A and 338B that prevent the sleeve 332 from falling out from the guide hole 330, and regulate a movable range of the sleeve 332. The stopper portions 338A and 338B are respectively provided with openings 340A and 340B through which the treatment tool insertion part 202 can be inserted. That is, an inner diameter D4 of each of the openings 340A and 340B is formed to be larger than the outer diameter D2 of the treatment tool insertion part 202, and smaller than the outer diameter D3 of the sleeve 332. Thus, if the treatment tool insertion part 202 moves back and forth in a state where the sleeve 332 is held to an outer circumference part of the treatment tool insertion part 202, the slider 308 does not move back and forth in a case where the back-and-forth movement of the treatment tool insertion part 202 (sleeve 332) is within a range of the allowance (a movable range regulated by the stopper portions 338A and 338B) of the slider 308. On the other hand, if the treatment tool insertion part 202 moves back and forth over the range of the allowance of the slider 308, the sleeve 332 held to the treatment tool insertion part 202 abuts on the stopper portion 338A or 338B, and the slider 308 moves back and forth integrally with the treatment tool insertion part 202.

The position sensor 310 detects the movement amount of the slider 308 that is movable in interlock with the back-and-forth movement of the treatment tool insertion part 202, with an allowance with respect to the movement of the treatment tool insertion part 202. That is, the position sensor 310 is configured as detection means that has a non-sensitive area where a change of a relative position of the treatment tool insertion part 202 with respect to the endoscope insertion part 102 is not detected even if the treatment tool insertion part 202 moves back and forth, and a sensitive area where a change of the relative position of the treatment tool insertion part 202 is detected if the treatment tool insertion part 202 moves back and forth, and that detects a movement amount of the treatment tool insertion part 202 with respect to the outer tube body 302 in the sensitive area. As the position sensor 310, a position sensor, such as a potentiometer, an encoder, and a magnetic resistance (MR) sensor, can be used. For example, as shown in FIG. 3, by detecting an rotation amount of a rotation body (roller) configured to be rotatable according to the back-and-forth movement of the slider 308 using a rotary encoder, a potentiometer, or the like, it is possible to detect the movement amount of the slider 308. The detection result of the position sensor 310 is output to the control unit 314.

Here, it is assumed that the movement amount of the slider 308 detected by the position sensor 310 has a positive or negative value depending on a movement direction. Specifically, the movement amount of the slider 308 is indicated as a positive value in a case where the slider 308 moves to a diseased part side (a distal end side or a forward side) in a body cavity, and the movement amount of the slider 308 is indicated as a negative value in a case where the slider 308 moves to a hand side (a proximal end side or a backward side) opposite to the diseased part side.

The endoscope drive unit 312 is drive means that moves the endoscope insertion part 102 inserted into the endoscope insertion path 304 back and forth, and that is composed of a motor, a gear, and the like, for example. The endoscope drive unit 312 moves the endoscope insertion part 102 back and forth on the basis of a control signal outputted from the control unit 314. Although the endoscope drive unit 312 is built in the outer tube body 302 in the present example, but it is not limited to this, the endoscope drive unit may be one which moves back and forth the endoscope insertion part 102 from outside of the outer tube body 302.

The control unit 314 is endoscope movement control means that controls back-and-forth movement of the endoscope insertion part 102 through the endoscope drive unit 312 on the basis of a detection result of the position sensor 310. That is, the control unit 314 controls the back-and-forth movement of the endoscope insertion part 102 in accordance with the movement amount of the slider 308, and moves the endoscope insertion part 102 back and forth with an allowance with respect to the movement of the treatment tool insertion part 202, in interlock with the back-and-forth movement of the treatment tool insertion part 202. The control unit 314 may be built in the outer tube body 302, or may be connected to the outside of the outer tube body 302 through wiring.

Figure 5:
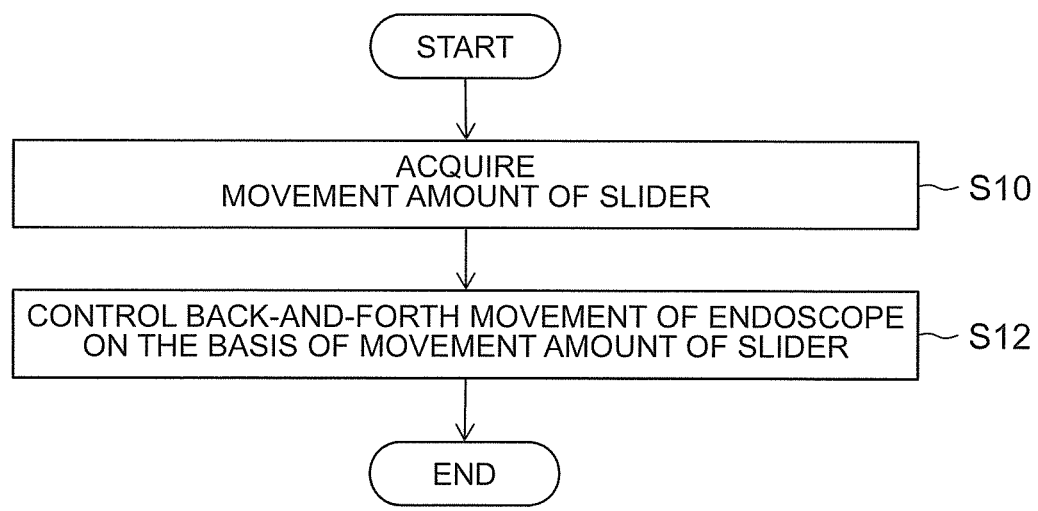
FIG. 5 is a flow chart showing an example of processing performed by a control unit.

FIG. 5 is a flow chart showing an example of processing performed by the control unit 314.

First, the control unit 314 acquires the movement amount of the slider 308 detected by the position sensor 310 (step S10).

Next, the control unit 314 controls the endoscope insertion part 102 so as to move back and forth through the endoscope drive unit 312 on the basis of the movement amount of the slider 308 acquired from the position sensor 310 (step S12). Specifically, the control unit 314 outputs a control signal for moving the endoscope insertion part 102 back and forth by the same movement amount as the movement amount of the slider 308, to the endoscope drive unit 312. Then, the endoscope drive unit 312 moves the endoscope insertion part 102 back and forth on the basis of the control signal supplied from the control unit 314. Accordingly, the endoscope insertion part 102 moves back and forth in interlock with movement of the slider 308 by the same movement amount as the movement amount of the slider 308, that is, moves back and forth with an allowance with respect to the movement amount of the treatment tool insertion part 202, in interlock with (synchronously with) the treatment tool insertion part 202.

Figure 6:
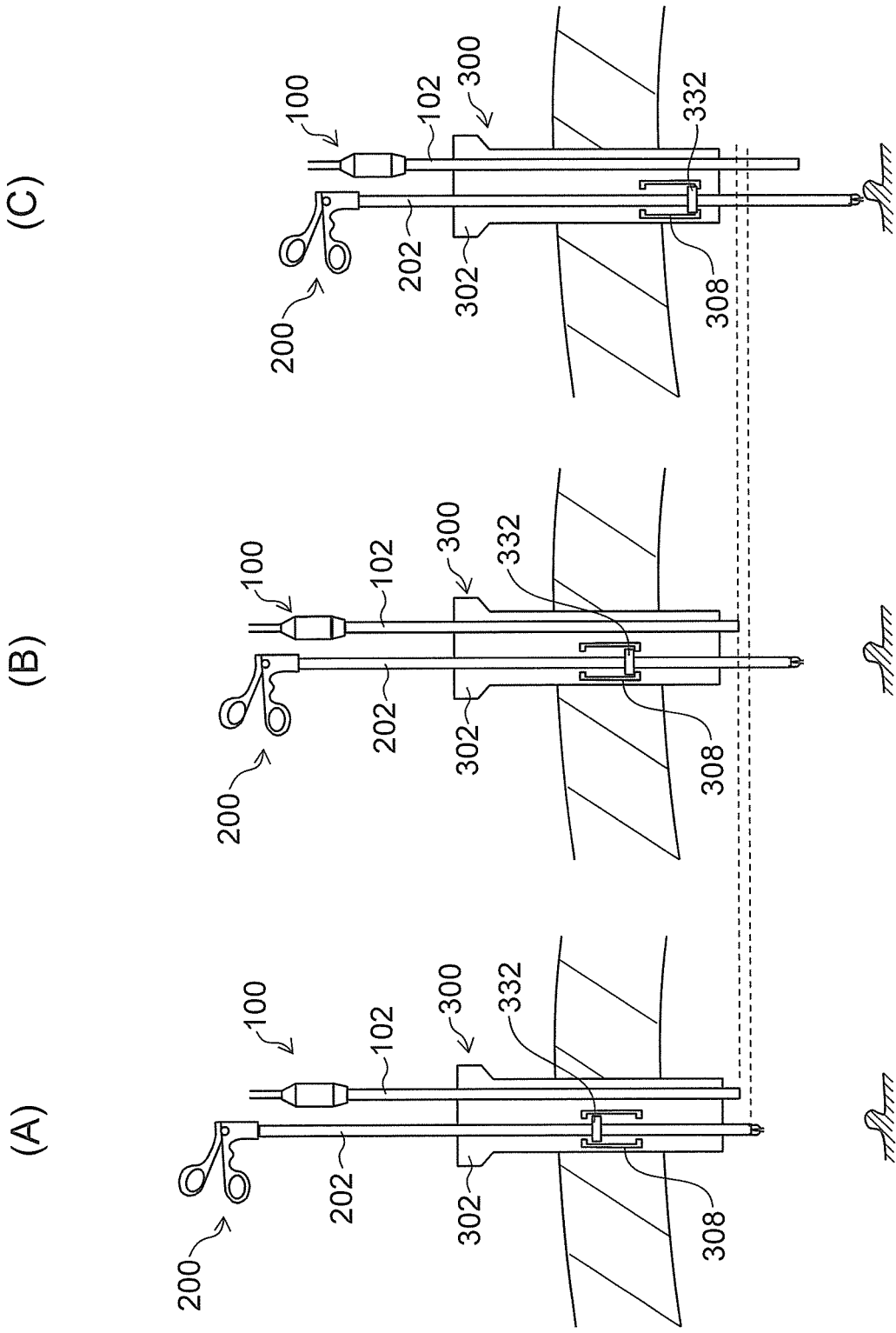
FIG. 6 is a diagram showing a state where an insertion part of a treatment tool is pushed into a diseased part side in a body cavity from a hand side.
Figure 7:
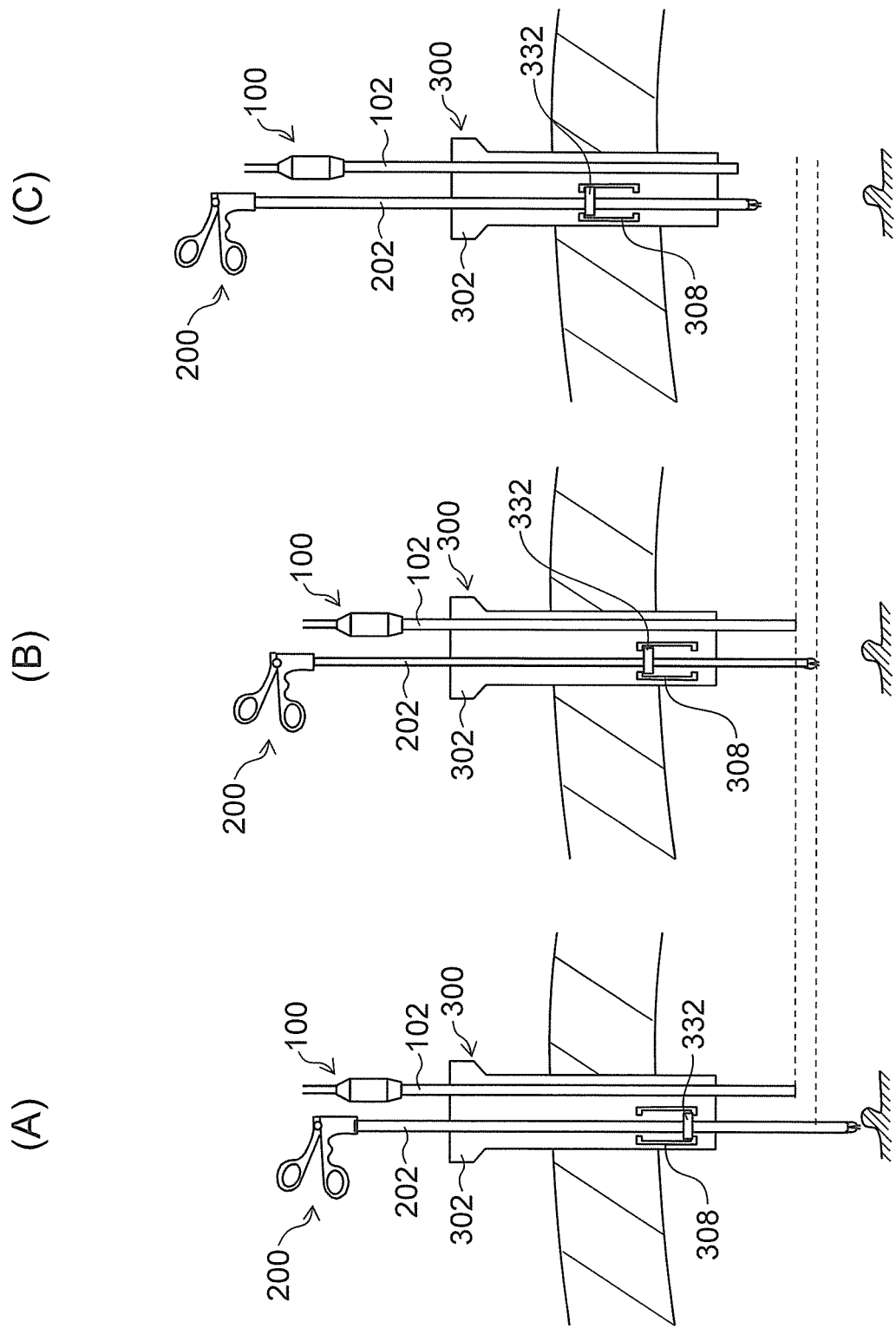
FIG. 7 is a diagram showing a state where an insertion part of a treatment tool is pulled from a diseased part side in a body cavity to a hand side.

Each of FIGS. 6 and 7 is an illustration showing a state where the endoscopic surgery device 10 of the present embodiment is operated. FIG. 6 is a diagram showing a state where the treatment tool insertion part 202 is pushed into a diseased part side in a body cavity from a hand side. FIG. 7 is a diagram showing a state where the treatment tool insertion part 202 is pulled from a diseased part side in a body cavity to a hand side. Hereinafter, first a preparation process for starting operation of the endoscopic surgery device 10 will be described, and then action at the time when the operation shown in FIGS. 6 and 7 is performed will be described.

First, as the preparation process for starting operation of the endoscopic surgery device 10, the outer tube body 302 is inserted into a body cavity through an opening (incised wound) formed in a body wall, and then the treatment tool insertion part 202 is inserted into the treatment tool insertion path 306 from the treatment tool entry port 324 so that a distal end of the treatment tool insertion part 202 is delivered out from the treatment tool exit port 326. At this time, the treatment tool insertion part 202 passes through the treatment tool holding hole 334 of the sleeve 332 provided inside the slider 308. As described above, since the inner diameter D1 of the treatment tool holding hole 334 is formed to be slightly smaller than the outer diameter D2 of the treatment tool insertion part 202 (refer to FIGS. 3 and 4), the sleeve 332 is held is a state where the sleeve 332 is brought into close contact with the treatment tool insertion part 202 by elastic force of the elastic member 336. Accordingly, the sleeve 332 becomes movable integrally with the treatment tool insertion part 202.

Subsequently, the endoscope insertion part 102 is inserted into the endoscope insertion path 304 from the endoscope entry port 318, and then a distal end of the endoscope insertion part 102 is delivered out from the endoscope exit port 322. At this time, the endoscope insertion part 102 is adjusted so as to arrange a position of the distal end of the endoscope insertion part 102, at least, on the back side (on the hand side opposite to the diseased part side in the body cavity) of a position of the distal end of the treatment tool insertion part 202. Accordingly, a state of the treatment part 206 arranged at the distal end of the treatment tool insertion part 202 can be observed with the endoscope 100.

After the preparation process is performed in this way, the endoscopic surgery device 10 becomes a state where operation thereof can be started. Here, insertion procedure of the endoscope 100 and the treatment tool 200 into the outer tube body 302 is not limited to the order described above, and the treatment tool 200 may be inserted followed by the endoscope 100.

Next, a state where the treatment tool insertion part 202 is pushed into the diseased part side in the body cavity from the hand side will be described with reference to FIG. 6.

First, in a case where the treatment tool insertion part 202 is slightly displaced in the axial direction (in a case where the back-and-forth movement of a small amplitude is performed) as a state changes from a state shown in portion (A) of FIG. 6 to a state shown in portion (B) of FIG. 6, only the treatment tool insertion part 202 moves back and forth and the slider 308 does not move back and forth. Thus, the output of the position sensor 310 that detects the movement amount of the slider 308 becomes zero. In this case, since the endoscope insertion part 102 does not move back and forth, a range of an observation image displayed in the monitor 112 does not change. As a result, it is possible to prevent a size of an observation target from changing in accordance with a slight displacement of the treatment tool insertion part 202, and thus a depth perception can be properly kept to enable a stable observation image to be acquired.

On the other hand, in a case where the treatment tool insertion part 202 is largely displaced in the axial direction (in a case where back-and-forth movement of a large amplitude is performed) as a state changes from a state shown in portion (A) of FIG. 6 to a state shown in portion (C) of FIG. 6, the slider 308 moves back and forth in interlock with the back-and-forth movement of the treatment tool insertion part 202. In this case, since the endoscope insertion part 102 moves back and forth, a range of an observation image displayed in the monitor 112 is continuously changed so as to follow the back-and-forth movement of the treatment tool insertion part 202. Accordingly, a size of an observation target is changed in response to operation of the treatment tool 200, so that it is possible to easily acquire an image desired by a surgeon.

The same applies to a case where the treatment tool insertion part 202 is pulled from the diseased part side in the body cavity to the hand side.

That is, in a case where the treatment tool insertion part 202 is slightly displaced in the axial direction (in a case of the back-and-forth movement of a small amplitude is performed) as a state changes from that shown in portion (A) of FIG. 7 to that shown in portion (B) of FIG. 7, only the treatment tool insertion part 202 moves back and forth and the slider 308 does not move back and forth. Thus, the output of the position sensor 310 that detects the movement amount of the slider 308 becomes zero. In this case, since the endoscope insertion part 102 does not move back and forth, a range of an observation image displayed in the monitor 112 does not change. As a result, it is possible to prevent a size of an observation target from changing in accordance with a slight displacement of the treatment tool insertion part 202, and thus a depth perception can be properly kept to enable a stable observation image to be acquired.

On the other hand, in a case where the treatment tool insertion part 202 is largely displaced in the axial direction (in a case where the back-and-forth movement of a large amplitude is performed) as a state changes from that shown in portion (A) of FIG. 7 to that shown in portion (C) of FIG.

7, the slider 308 moves back and forth in interlock with the back-and-forth movement of the treatment tool insertion part 202. In this case, since the endoscope insertion part 102 moves back and forth, a range of an observation image displayed in the monitor 112 is continuously changed so as to follow the back-and-forth movement of the treatment tool insertion part 202. Accordingly, a size of an observation target is changed in response to operation of the treatment tool 200, so that it is possible to easily acquire an image desired by a surgeon.

Here, it is preferable to control the back-and-forth movement of the endoscope insertion part 102 so that a range of an observation image displayed in the monitor 112 is always constant even if the treatment tool insertion part 202 is moved back and forth.

As above, in the present embodiment, in a state where the endoscope insertion part 102 and the treatment tool insertion part 202 are arranged in parallel, since the endoscope insertion part 102 moves back and forth with an allowance with respect to the back-and-forth movement of the treatment tool insertion part 202, a range of an observation image acquired by the endoscope 100 is changed. Accordingly, it is possible to prevent a size of an observation target from changing in a case where the treatment tool insertion part 202 is slightly displaced in the axial direction (in a case where the back-and-forth movement of a small amplitude is performed). As a result, a depth perception can be properly kept to enable a stable observation image to be provided. In addition, in a case where the treatment tool insertion part 202 is largely displaced in the axial direction (in a case where the back-and-forth movement of a large amplitude is performed), since a range of an observation image is changed in interlock with the displacement, a size of the observation target changes in response to the operation of the treatment tool 200. As a result, it is possible to easily acquire an image desired by a surgeon and operability is improved.

Particularly in the present embodiment, in a case where the treatment tool insertion part 202 is largely displaced in the axial direction, since a range of an observation image is continuously changed in interlock with the back-and-forth movement of the treatment tool insertion part 202 without being discretely changed, the observation image smoothly changes in response to operation of the treatment tool 200. As a result, a surgeon can operate the treatment tool 200 without a sense of discomfort while viewing the observation image.

In addition, since the surgeon can change a range of an observation image acquired by the endoscope 100 by only operating the treatment tool 200 without releasing its hand from the treatment tool 200, operation of the endoscope 100 by an assistant becomes unnecessary. As a result, it is possible to display a part where the surgeon wants to view without stress, and eliminate stress caused by an assistant and instruction time for the assistant, so that operative procedure becomes easy to enable operative time to be shortened.

Second Embodiment

Next, a second embodiment of the present invention will be described. Hereinafter, description of a portion common to the first embodiment is omitted, and the present embodiment will be described with a focus on characteristics thereof.

Figure 8:
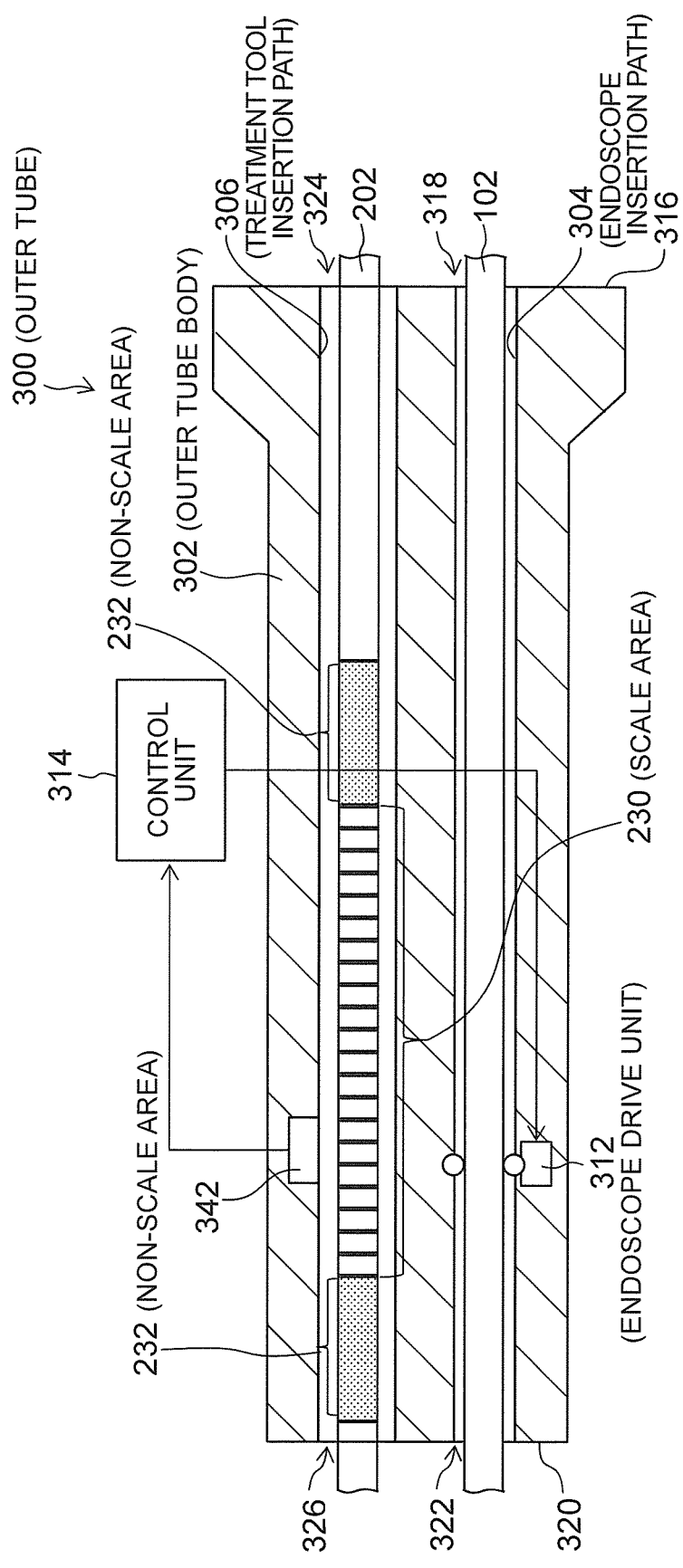
FIG. 8 is a schematic configuration diagram showing a structure of a main part of an endoscopic surgery device according to a second embodiment.

FIG. 8 is a schematic configuration diagram showing a structure of a main part of an endoscopic surgery device according to the second embodiment. In FIG. 8, a component that is identical with or corresponds to that of Figures shown above is designated by the same reference numeral as that of the Figures.

In the second embodiment, as shown in FIG. 8, an outer peripheral surface of the treatment tool insertion part 202 is provided with a scale area 230 where a movement amount of the treatment tool insertion part 202 with respect to the outer tube body 302 can be detected by a detection sensor 342 described later, and with a non-scale area 232 where the movement amount above is not detected.

The scale area 230 includes high density parts and low density parts that are alternately repeated along the axial direction of the treatment tool insertion part 202.

The non-scale area 232 includes uniform density parts each having a uniform density along the axial direction of the treatment tool insertion part 202, and the uniform density parts are formed at both sides of the scale area 230 (or a distal end side and a proximal end side of the treatment tool insertion part 202 in the axial direction).

Inside the outer tube body 302, there is provided the detection sensor 342 as detection means which detects a change in a relative position of the treatment tool insertion part 202 with respect to the endoscope insertion part 102 when the treatment tool insertion part 202 moves back and forth. The detection sensor 342 is optical reading means which optically reads the high density parts and the low density parts of the scale area 230 formed around the treatment tool insertion part 202, and is configured by a light emission element and a light-receiving element, for example. In a case where the scale area 230 passes through a position facing the detection sensor 342 when the treatment tool insertion part 202 moves back and forth, for example, the detection sensor 342 detects the movement amount of the treatment tool insertion part 202. On the other hand, in a case where the non-scale area 232 passes through the position facing the detection sensor 342, the detection sensor 342 does not detect the movement amount of the treatment tool insertion part 202. The detection result of the detection sensor 342 is output to the control unit 314.

Here, the detection sensor 342 is not limited to the optical reading means, and the detection sensor 342 may be configured by reading means capable of magnetically or electronically reading, for example. In this case, the outer peripheral surface of the treatment tool insertion part 202 is provided with scale information corresponding to the reading means.

The control unit 314 controls the endoscope drive unit 312 on the basis of the detection result of the detection sensor 342. That is, the control unit 314 controls the endoscope insertion part 102 so as to move through the endoscope drive unit 312 in accordance with the movement amount of the treatment tool insertion part 202 detected by the detection sensor 342.

Figure 9:
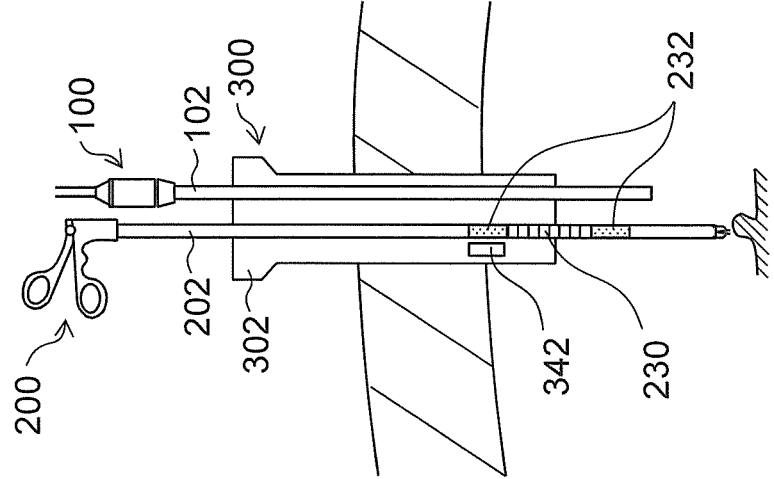
FIG. 9 is a diagram showing a state where an endoscopic surgery device according to the second embodiment is operated.
Figure 9:
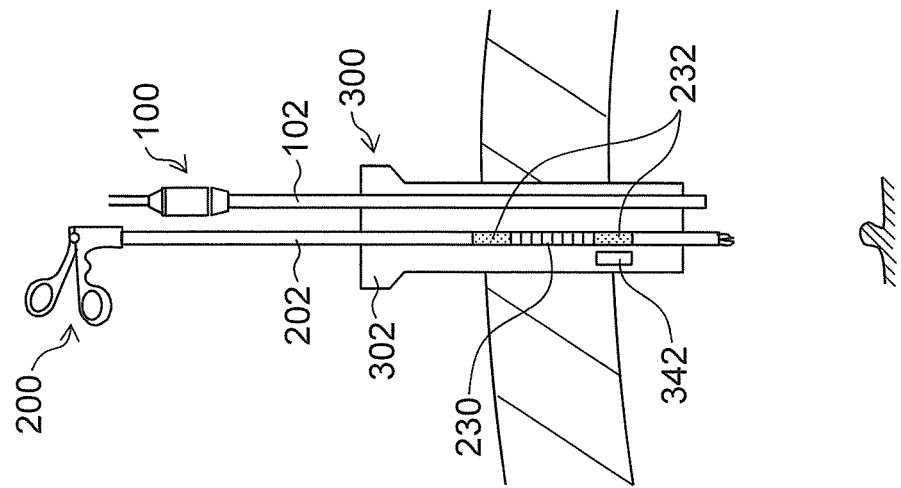

By the configuration described above, the endoscope insertion part 102 does not move back and forth in a case where the treatment tool insertion part 202 is slightly displaced in the axial direction (in a case where the back-and-forth movement of a small amplitude is performed), in a state where the treatment tool insertion part 202 is pulled to the hand side as shown in portion (A) of FIG. 9, and in a state where the treatment tool insertion part 202 is pushed to a diseased part side in a body cavity as shown in portion (B) of FIG. 9. Thus, a range of an observation image displayed in the monitor 112 does not change. As a result, it is possible to prevent a size of an observation target from changing in accordance with a slight displacement of the treatment tool insertion part 202, so that a depth perception can be properly kept to enable a stable observation image to be acquired.

On the other hand, in a case where the treatment tool insertion part 202 is largely displaced in the axial direction (in a case of back-and-forth movement of a large amplitude is performed), the endoscope insertion part 102 moves back and forth in interlock with the back-and-forth movement of the treatment tool insertion part 202. Accordingly, a range of an observation image displayed in the monitor 112 is continuously changed so as to follow the back-and-forth movement of the treatment tool insertion part 202. As a result, a size of an observation target is changed in response to operation of the treatment tool 200, so that it is possible to easily acquire an image desired by a surgeon.

According to the second embodiment, the detection sensor 342 can detect the movement amount of the treatment tool insertion part 202, with an allowance with respect to the back-and-forth movement of the treatment tool insertion part 202. Accordingly, it is possible to allow the endoscope insertion part 102 to move back and forth in interlock with the back-and-forth movement of the treatment tool insertion part 202 with an allowance, so that the same effect as that of the first embodiment can be obtained.

Third Embodiment

Next, a third embodiment of the present invention will be described. Hereinafter, description of a portion common to the first and second embodiments is omitted, and the present embodiment will be described with a focus on characteristics thereof.

Figure 10:
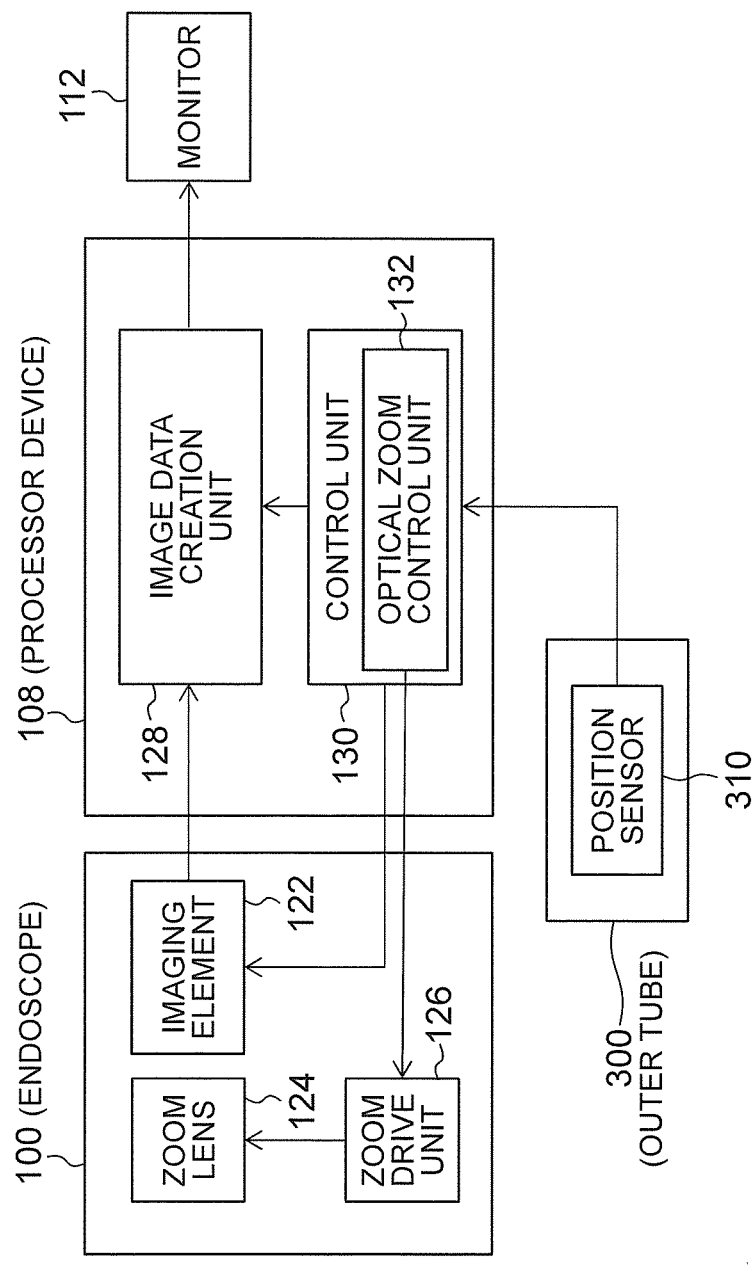
FIG. 10 is a functional block diagram showing a configuration of a main part of an endoscopic surgery device according to a third embodiment.

FIG. 10 is a functional block diagram showing a configuration of a main part of an endoscopic surgery device according to the third embodiment. In FIG. 10, a component that is identical with or corresponds to that of Figures shown above is designated by the same reference numeral as that of the Figures.

In the third embodiment, as shown in FIG. 10, an observation optical system of the endoscope 100 includes a zoom lens 124 as a part of lenses thereof. The zoom lens 124 is configured to be movable in an optical axis direction with a zoom drive unit 126. The zoom lens 124 is moved in the optical axis direction to change a focal length so that magnification of a subject image imaged in an imaging element 122 is changed. As a result, the magnification of the observation image displayed in the monitor 112 is changed.

The processor device 108 is provided with an image data creation unit 128 that applies various kinds of signal processing, such as color separation, color interpolation, gain correction, white balance adjustment, and gamma correction, to an imaging signal outputted from the imaging element 122 of the endoscope 100 to create image data. The image data created by the image data creation unit 128 is converted into a video signal in accordance with a signal type corresponding to the monitor 112 to be outputted to the monitor 112. Accordingly, an observation image (endoscope image) is displayed in the monitor 112.

In addition, the processor device 108 is provided with a control unit 130 that integrally controls the processor device 108 and each unit of the endoscope 100. The control unit 130 includes an optical zoom control unit 132 as optical zoom control means. The optical zoom control unit 132 controls the zoom lens 124 so as to move in the optical axis direction through the zoom drive unit 126 on the basis of a detection result (that is, a movement amount of the slider 308) of a position sensor 310 provided in the outer tube 300. Accordingly, the zoom lens 124 moves in the optical axis direction to change a focal length, so that magnification of a subject image imaged in the imaging element 122 is changed.

The position sensor 310, as described in the first embodiment, is detection means which detects a movement amount of slider 308 that moves in interlock with a back-and-forth movement of the treatment tool insertion part 202, with an allowance with respect to the movement of the treatment tool insertion part 202.

By the configuration described above, in a case where the treatment tool insertion part 202 is slightly displaced in the axial direction (in a case of a back-and-forth movement of a small amplitude is performed), the zoom lens 124 is not driven. Thus, a range of an observation image displayed in the monitor 112 does not change. As a result, it is possible to prevent a size of an observation target from changing, and a depth perception can be properly kept to enable a stable observation image to be provided. On the other hand, in a case where the treatment tool insertion part 202 is largely displaced in the axial direction (in a case of a back-and-forth movement of a large amplitude is performed), the zoom lens 124 is driven in interlock with the back-and-forth movement of the treatment tool insertion part 202. As a result, since a range of an observation image displayed in the monitor 112 is continuously changed so as to follow the back-and-forth movement of the treatment tool insertion part 202, a size of an observation target changes in response to operation of the treatment tool 200, and thus an image desired by a surgeon can be easily acquired and operability is improved.

In addition, it is preferable to control drive of the zoom lens 124 so that a range of an observation image displayed in the monitor 112 is always constant even if the treatment tool insertion part 202 is moved back and forth.

Thus, also in the third embodiment, the same effect as that of the first embodiment can be obtained. In addition, since it is unnecessary to provide means (such as the endoscope drive unit 312) for moving the endoscope insertion part 102 inserted into the endoscope insertion path 304 back and forth, a structure of the outer tube body 302 becomes simple to enable a diameter of the outer tube body 302 to be reduced.

Fourth Embodiment

Next, a fourth embodiment of the present invention will be described. Hereinafter, description of a portion common to the first to third embodiments is omitted, and the present embodiment will be described with a focus on characteristics thereof.

Figure 11:
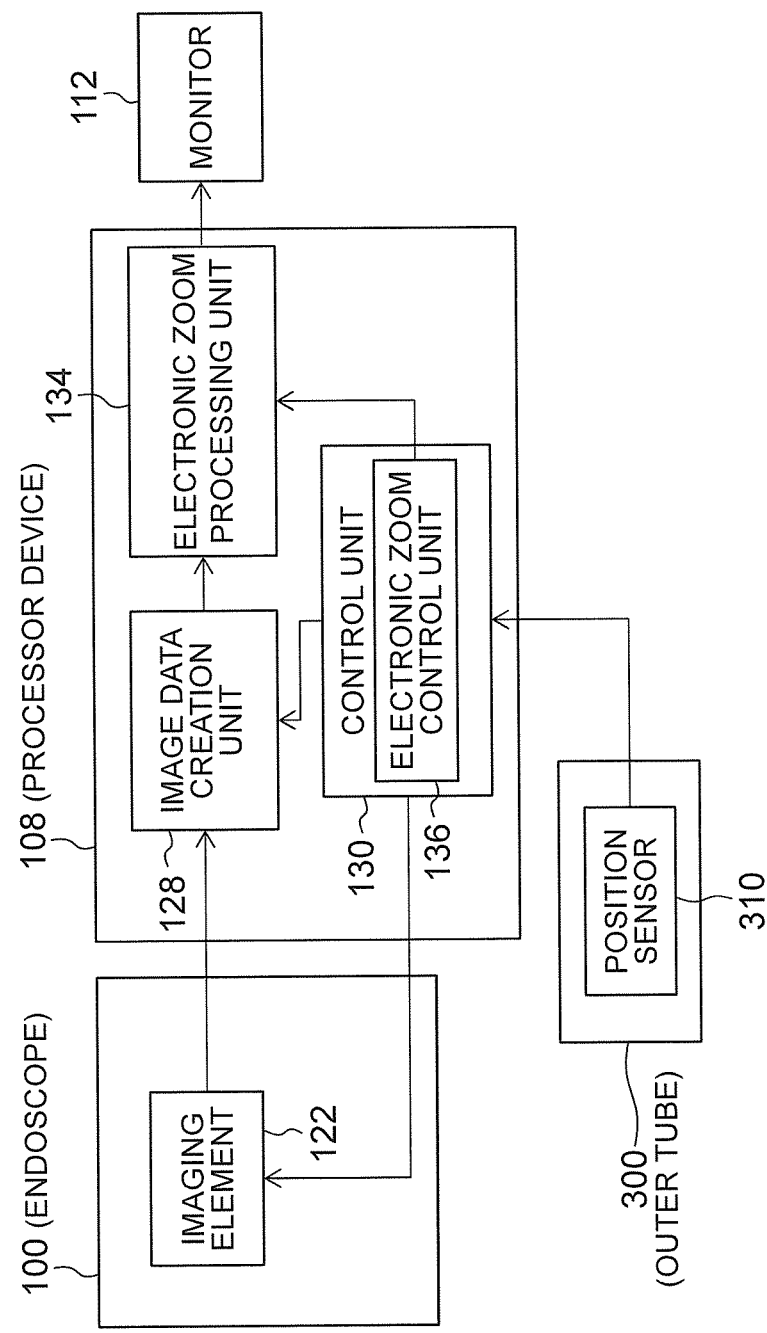
FIG. 11 is a functional block diagram showing a configuration of a main part of an endoscopic surgery device according to a fourth embodiment.

FIG. 11 is a functional block diagram showing a configuration of a main part of an endoscopic surgery device according to the fourth embodiment. In FIG. 11, a component that is identical with or corresponds to that of Figures shown above is designated by the same reference numeral as that of the Figures.

In the fourth embodiment, as shown in FIG. 11, the processor device 108 includes an electronic zoom processing unit 134 that extracts a part of image data created by the image data creation unit 128 to electronically perform variable magnification processing.

The control unit 130 includes an electronic zoom control unit 136 as electronic zoom control means. The electronic zoom control unit 136 changes magnification of an observation image displayed in the monitor 112 by controlling the electronic zoom processing unit 134 on the basis of a detection result (that is, a movement amount of the slider 308) of the position sensor 310 provided in the outer tube 300.

By the configuration described above, in a case where the treatment tool insertion part 202 is slightly displaced in the axial direction (in a case of a back-and-forth movement of a small amplitude is performed), since the electronic zoom processing unit 134 does not perform the variable magnification processing, a range of an observation image displayed in the monitor 112 does not change. As a result, it is possible to prevent a size of an observation target from changing, so that a depth perception can be properly kept and a stable observation image can be provided. On the other hand, in a case where the treatment tool insertion part 202 is largely displaced in the axial direction (in a case of a back-and-forth movement of a large amplitude is performed), the electronic zoom processing unit 134 performs the variable magnification processing in interlock with the back-and-forth movement of the treatment tool insertion part 202. As a result, since a range of an observation image displayed in the monitor 112 is continuously changed so as to follow the back-and-forth movement of the treatment tool insertion part 202, a size of an observation target changes in response to the operation of the treatment tool 200 to enable an image desired by a surgeon to be easily acquired and operability is improved.

Here, it is preferable to control the variable magnification processing by the electronic zoom processing unit 134 so that a range of an observation image displayed in the monitor 112 is always constant even if the treatment tool insertion part 202 is moved back and forth.

Thus, also in the fourth embodiment, the same effect as that of the first embodiment can be obtained. In addition, since it is unnecessary to provide means (such as the endoscope drive unit 312) for moving the endoscope insertion part 102 inserted into the endoscope insertion path 304 back and forth, a structure of the outer tube body 302 becomes simple to enable a diameter the outer tube body 302 to be reduced.

Fifth Embodiment

Next, a fifth embodiment of the present invention will be described. Hereinafter, description of a portion common to the first to fourth embodiments is omitted, and the present embodiment will be described with a focus on characteristics thereof.

Figure 12:
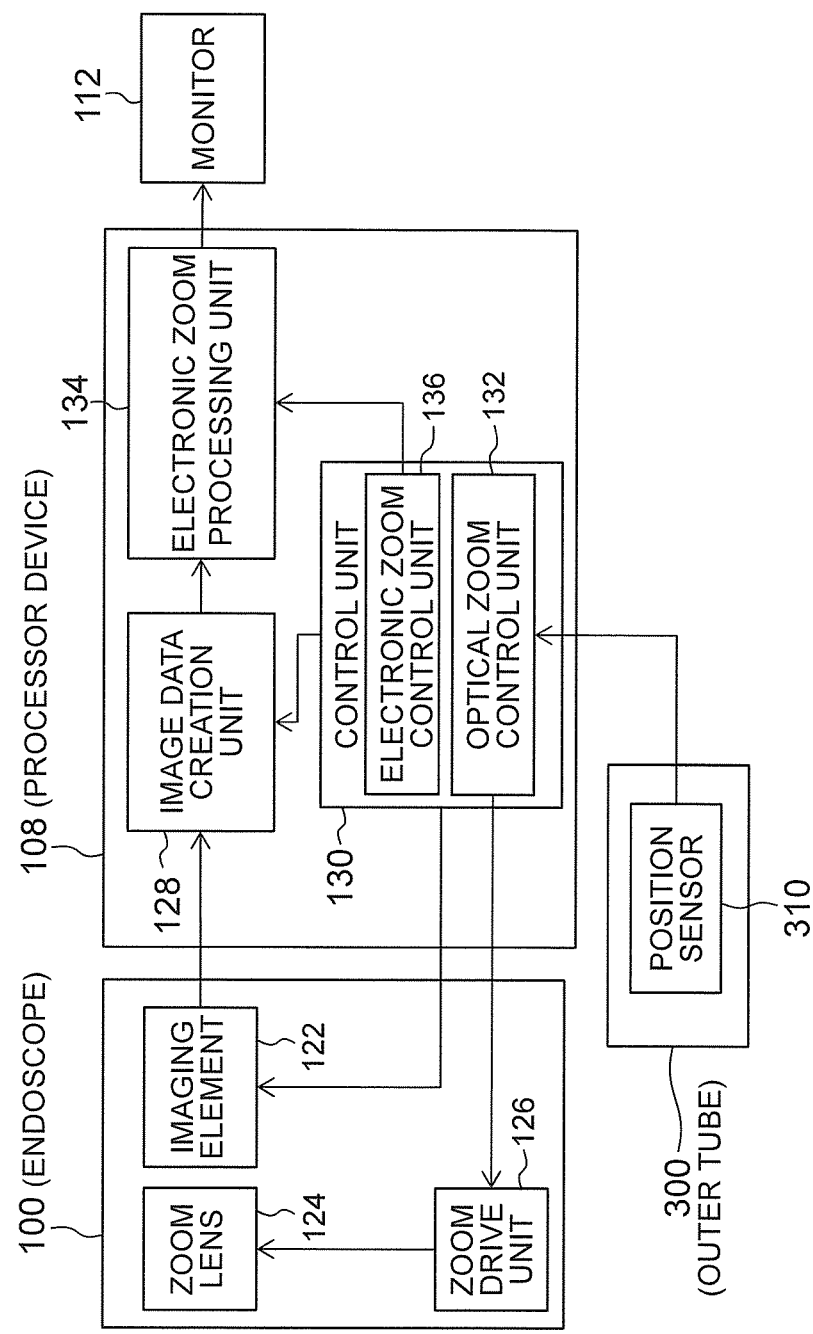
FIG. 12 is a functional block diagram showing a configuration of a main part of an endoscopic surgery device according to a fifth embodiment.

FIG. 12 is a functional block diagram showing a configuration of a main part of an endoscopic surgery device according to the fifth embodiment. In FIG. 12, a component that is identical with or corresponds to that of Figures shown above is designated by the same reference numeral as that of the Figures.

The fifth embodiment is an aspect of a combination of the third embodiment and the fourth embodiment. That is, as shown in FIG. 12, the control unit 130 of the processor device 108 includes the optical zoom control unit 132 and the electronic zoom control unit 136. The optical zoom control unit 132 controls movement of the zoom lens 124 through the zoom drive unit 126 on the basis of a detection result of the position sensor 310. The electronic zoom control unit 136 controls variable magnification processing by the electronic zoom processing unit 134 on the basis of the detection result of the position sensor 310.

According to the fifth embodiment, since the control unit 130 of the processor device 108 includes the optical zoom control unit 132 and the electronic zoom control unit 136, control in the optical zoom can be preferentially performed in a case where the endoscope 100 includes the zoom lens 124. On the other hand, in a case where the endoscope 100 includes no zoom lens 124, control in electronic zoom can be performed. Thus, regardless of types of the endoscope 100 (with or without the zoom lens 124), a range of an observation image displayed in the monitor 112 can be continuously changed so as to follow the back-and-forth movement of the treatment tool insertion part 202 with an allowance with respect to the back-and-forth movement of the treatment tool insertion part 202. Thus, the same effect as that of the first embodiment can be obtained.

Here, it is preferable to control the drive of the zoom lens 124 or the variable magnification processing by the electronic zoom processing unit 134 so that a range of an observation image displayed in the monitor 112 is always constant even if the treatment tool insertion part 202 is moved back and forth.

Although the third to fifth embodiments described above show a case where the position sensor 310 that detects the movement amount of the slider 308 is used as detection means that detects the movement amount of the treatment tool insertion part 202 with an allowance with respect to the back-and-forth movement of the treatment tool insertion part 202. However, the detection means is not limited to this. The detection sensor 342 of the second embodiment (refer to FIG. 8), a treatment tool movement amount detector 344 (refer to FIG. 13) in a sixth embodiment described later, and the like, can be used as the detection means.

Sixth Embodiment

Next, a sixth embodiment of the present invention will be described. Hereinafter, description of a portion common to the first to fifth embodiments is omitted, and the present embodiment will be described with a focus on characteristics thereof.

Figure 13:
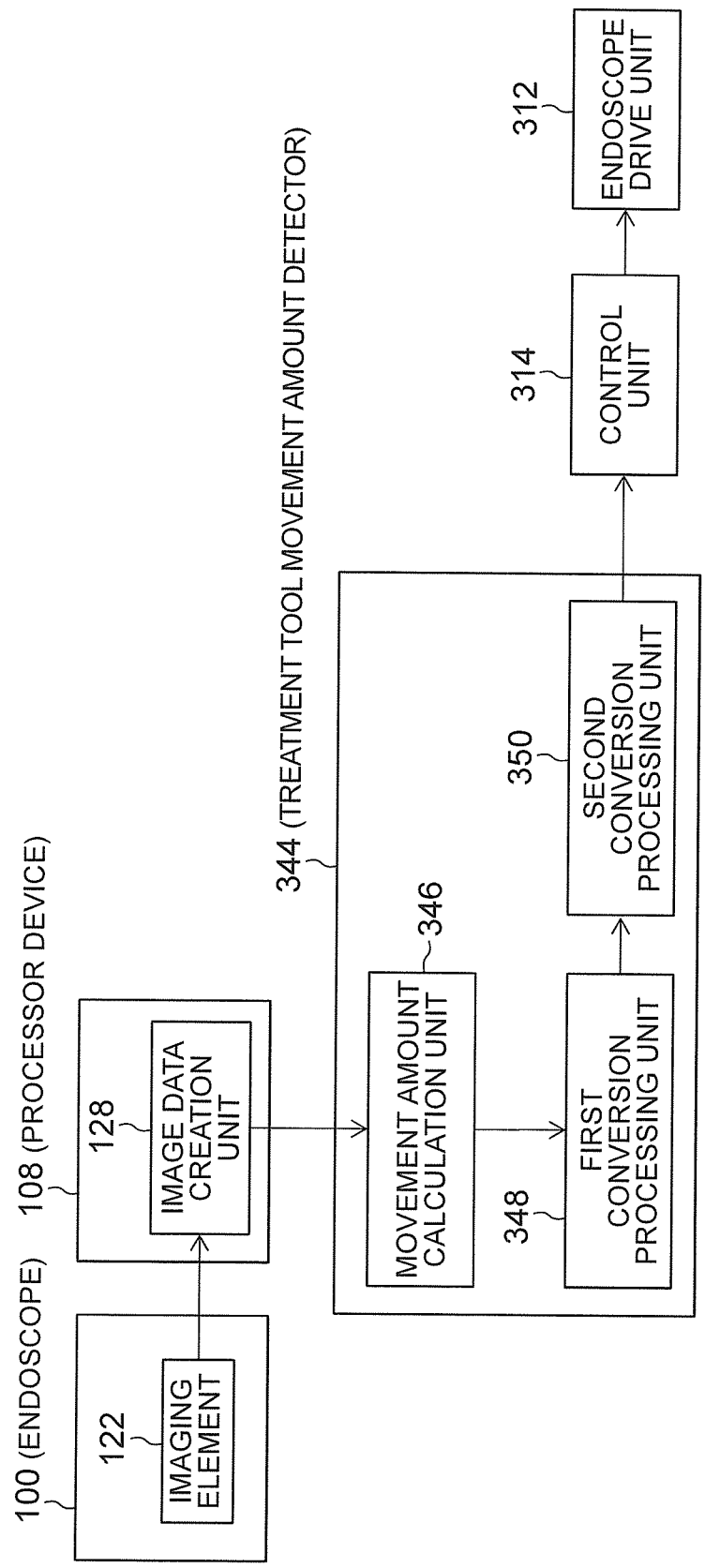
FIG. 13 is a functional block diagram showing a configuration of a main part of an endoscopic surgery device according to a sixth embodiment.

FIG. 13 is a functional block diagram showing a configuration of a main part of an endoscopic surgery device according to the sixth embodiment. In FIG. 13, a component that is identical with or corresponds to that of Figures shown above is designated by the same reference numeral as that of the Figures.

The sixth embodiment includes the treatment tool movement amount detector 344 as detection means that detects the movement amount of the treatment tool insertion part 202 with an allowance with respect to the back-and-forth movement of the treatment tool insertion part 202 on the basis of image data created by the image data creation unit 128. The treatment tool movement amount detector 344, as with the control unit 314, may be built in the outer tube body 302, or may be connected to the outside of the outer tube body 302 through wiring.

The treatment tool movement amount detector 344 includes a movement amount calculation unit 346 (calculation means), a first conversion processing unit 348 (first conversion means), and a second conversion processing unit 350 (second conversion means).

Figure 14:
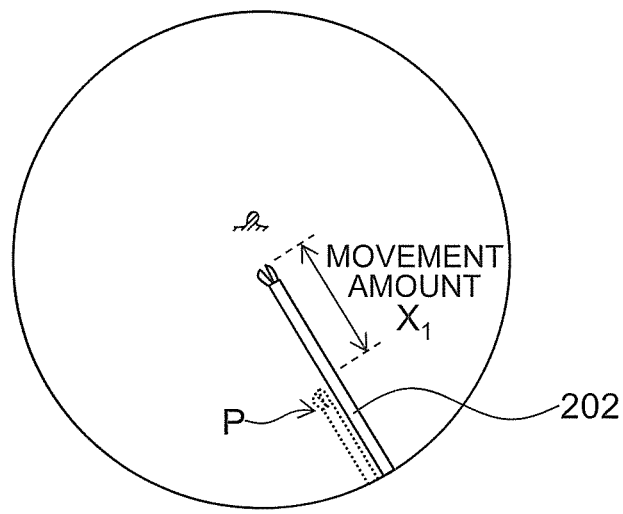
FIG. 14 is an illustration for describing a difference between a movement amount in an endoscope image and an actual movement amount.
Figure 14:
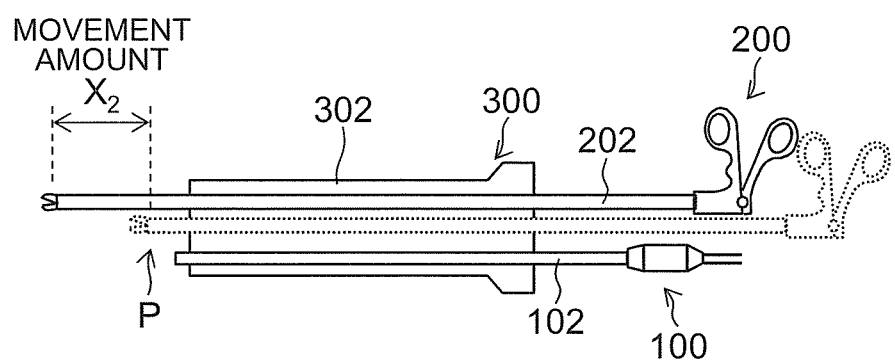

The movement amount calculation unit 346 calculates the movement amount of the treatment tool insertion part 202 on the basis of image data created by the image data creation unit 128. The movement amount calculated at this time is a movement amount $X_1$ in an observation image as shown in portion (A) of FIG. 14, and is different from an actual movement amount $X_2$ shown in portion (B) of FIG. 14. Here, a reference character P designates a starting position of movement of the treatment tool insertion part 202.

The first conversion processing unit 348 converts the movement amount $X_1$ in an observation image calculated by the movement amount calculation unit 346 into the actual movement amount $X_2$. Specifically, the first conversion processing unit 348 converts the movement amount $X_1$ in the observation image into the actual movement amount $X_2$ with reference to a look-up table. Here, a correspondence relationship between the movement amount $X_1$ in the observation image and the actual movement amount $X_2$ is uniquely determined from a clearance (distance) between the treatment tool insertion part 202 and the endoscope insertion part 102, an angle of view of the imaging element 122, or the like, and data showing the correspondence relationship is stored in a memory (not shown) as the look-up table.

Figure 15:
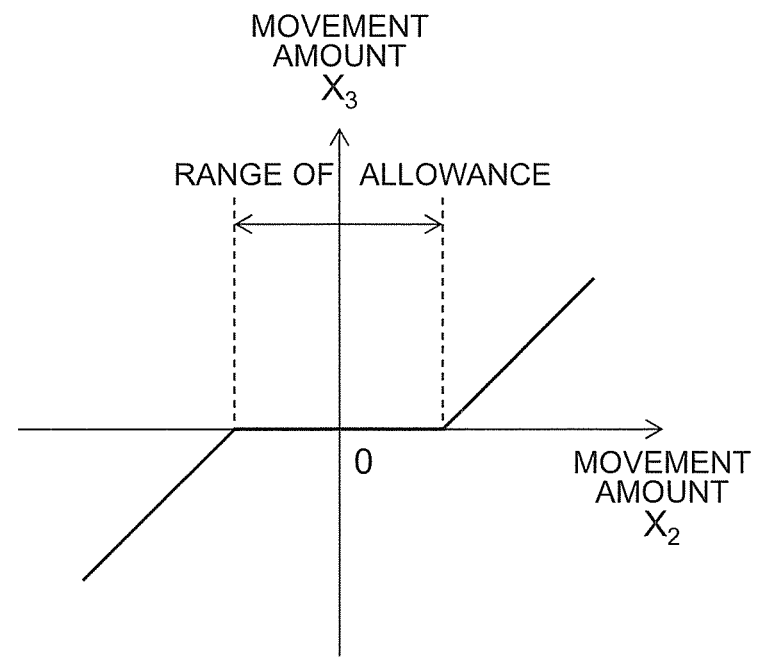
FIG. 15 is an illustration for describing conversion processing performed by a second conversion processing unit.

The second conversion processing unit 350 converts the movement amount (actual movement amount) $X_2$ of the treatment tool insertion part 202, which is acquired by the first conversion processing unit 348, into a movement amount $X_3$ to which a predetermined allowance is added. Specifically, conversion processing of the movement amount of the treatment tool insertion part 202 is performed according to a graph shown in FIG. 15. That is, if the movement amount $X_2$ of the treatment tool insertion part 202 is within a range of the allowance, the movement amount $X_3$ of the treatment tool insertion part 202 is set to zero. On the other hand, if the movement amount $X_2$ of the treatment tool insertion part 202 is not within the range of the allowance above, a value obtained by subtracting a predetermined value from the movement amount $X_2$ of the treatment tool insertion part 202 or a value obtained by adding a predetermined value to the movement amount $X_2$ is set as the movement amount $X_3$. The movement amount $X_3$ of the treatment tool insertion part 202 acquired as above is outputted to the control unit 314 as a detection result of the treatment tool movement amount detector 344.

The control unit 314 controls the back-and-forth movement of the endoscope insertion part 102 through the endoscope drive unit 312 on the basis of the detection result of the treatment tool movement amount detector 344.

According to the sixth embodiment, a movement amount at the time when the treatment tool insertion part 202 is moved back and forth, is detected with an allowance on the basis of image data. Thus, it becomes possible to move the endoscope insertion part 102 back and forth with an allowance with respect to the back-and-forth movement of the treatment tool insertion part 202, and the same effect as that of the first embodiment can be obtained.

Here, a range of an observation image displayed in the monitor 112 may be changed by optical zoom or electronic zoom, instead of by a back-and-forth movement of the endoscope insertion part 102, as with the third to fifth embodiments described above.

Seventh Embodiment

Next, a seventh embodiment of the present invention will be described. Hereinafter, description of a portion common to the first to sixth embodiments is omitted, and the present embodiment will be described with a focus on characteristics thereof.

Figure 16:
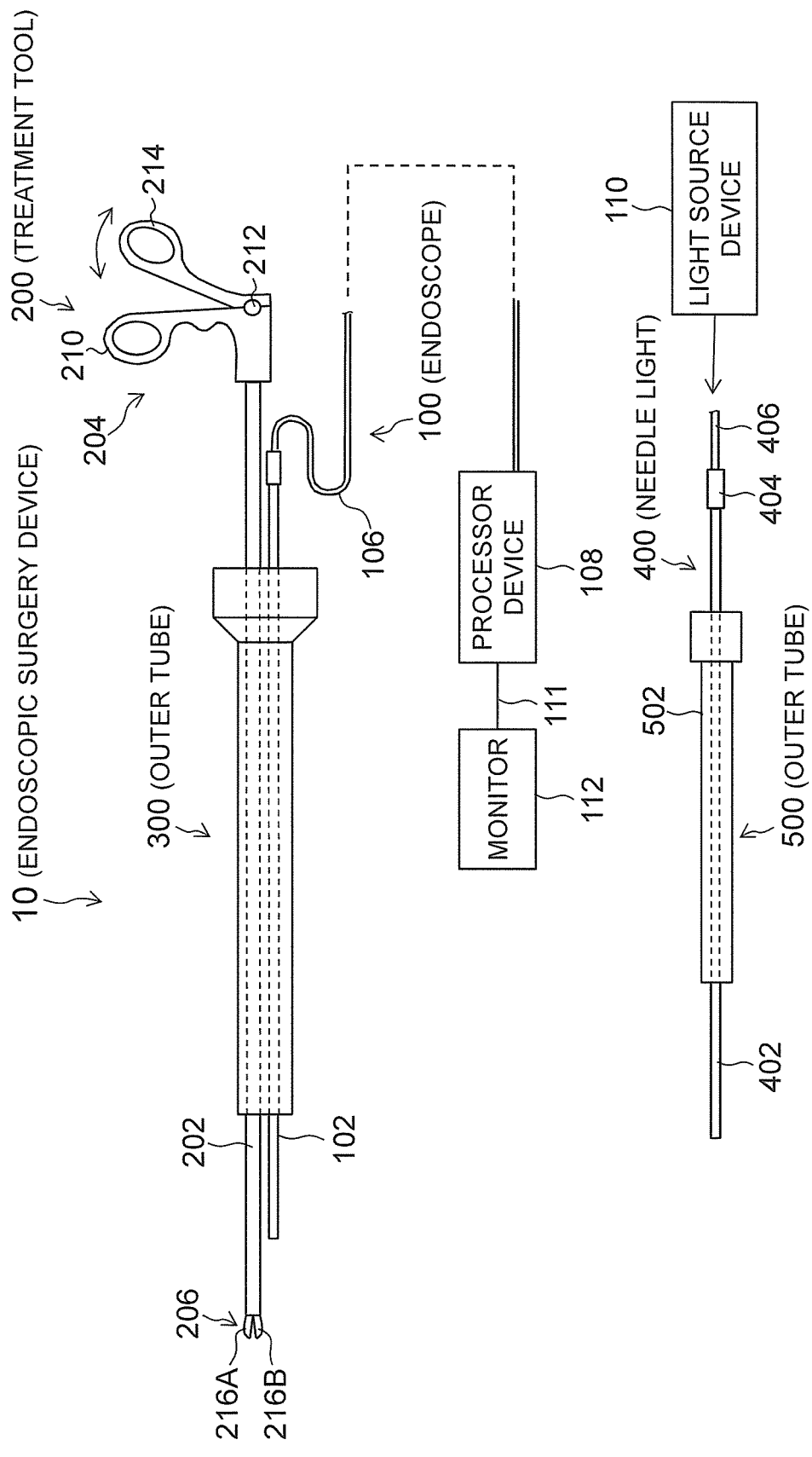
FIG. 16 is a schematic configuration diagram showing an endoscopic surgery device according to a seventh embodiment.

FIG. 16 is a schematic configuration diagram showing an endoscopic surgery device according to the seventh embodiment. In FIG. 16, a component that is identical with or corresponds to that of Figures shown above is designated by the same reference numeral as that of the Figures.

The seventh embodiment is different from the embodiments described above in that the endoscope 100 includes no illumination means for illuminating the inside of a body cavity. Thus, as shown in FIG. 16, the seventh embodiment includes a needle light 400 as a lighting for illuminating the inside of a body cavity, and an outer tube 500 which guides the needle light 400 into the body cavity.

The needle light 400 includes an elongated insertion part 402 that is to be inserted into a body cavity of a patient, a connection part 404 provided on a proximal end side of the insertion part 402, and a light cable 406 extending from a back end (proximal end side) of the connection part 404. The light cable 406 is provided at its end with a connector (not shown), and the connector is detachably connected to the light source device 110.

The insertion part 402 is provided in its distal end surface with an illumination window (not shown), and behind the illumination window, an emission end of a light guide (not shown) is arranged. The light guide is inserted into the insertion part 402, the connection part 404, and the light cable 406, and an incident end of the light cable 406 is arranged in a connector (not shown). Thus, when the connector is connected to the light source device 110, an illumination light from the light source device 110 is guided to the distal end side of the insertion part 402 through the light guide and emitted into a body cavity through the illumination window.

The outer tube 500 includes an outer tube body 502 that is a guide member to be penetrated through a body wall of a patient and inserted into the body cavity. Inside the outer tube body 502, there is provided an insertion path (not shown) formed so as to penetrate along an axial direction of the outer tube body 502. The insertion path is configured so that the insertion part 402 of the needle light 400 can be inserted (insertable) thereinto and movable back and forth.

Figure 17:
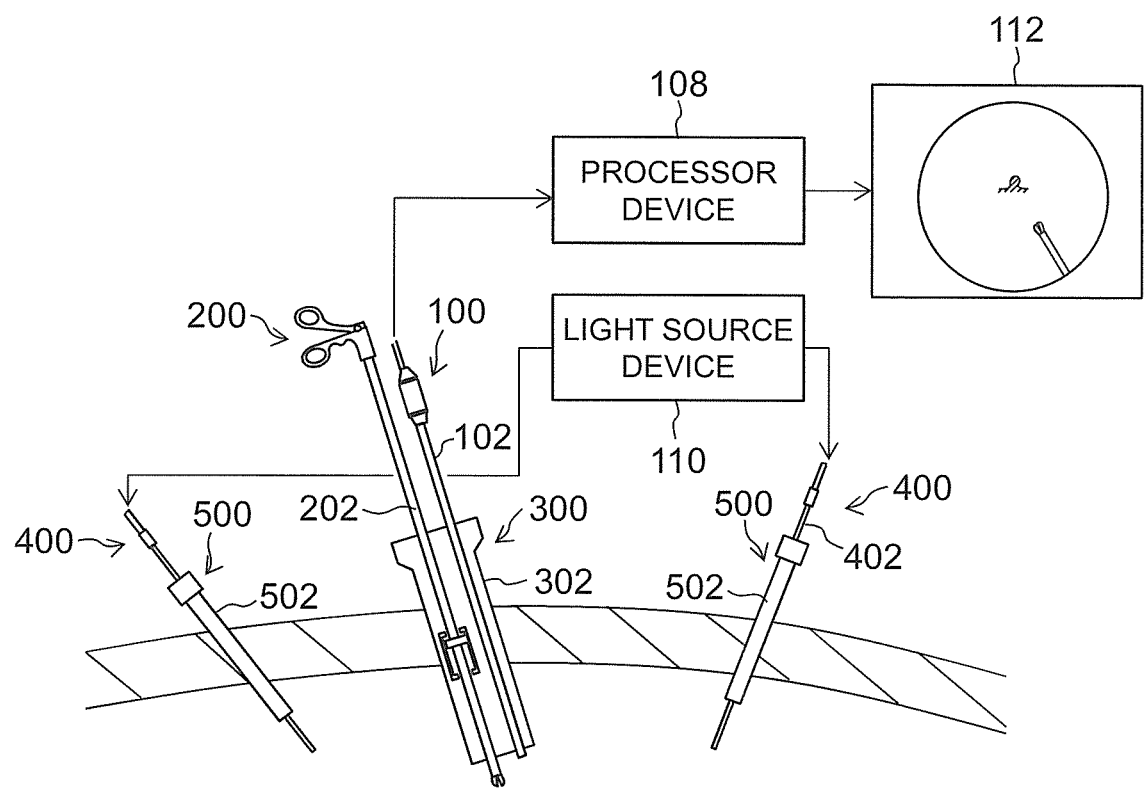
FIG. 17 is an explanation diagram showing a state where an endoscopic surgery device according to the seventh embodiment is used.

FIG. 17 is an explanation diagram showing a state where an endoscopic surgery device according to the seventh embodiment is used. In FIG. 17, a component that is identical with or corresponds to that of Figures shown above is designated by the same reference numeral as that of the Figures.

In the seventh embodiment, since the endoscope 100 includes no illumination means for illuminating the inside of a body cavity, one or more needle lights 400 are used in a case where an operation is performed by using the endoscope 100 and the treatment tool 200 which are guided into the body cavity through the outer tube 300, as shown in FIG. 17. FIG. 17 shows a case where the needle lights 400 and 400 are used.

The needle lights 400 are guided into the body cavity in a state where the needle rights are inserted into an insertion path (not shown) of the outer tube bodies 502 that penetrate a body wall. Then, illumination light from the light source device 110 is supplied to each of the needle lights 400, and the illumination light is emitted into the body cavity through an illumination window (not shown) provided in a distal end surface of the needle light 400.

According to the seventh embodiment, desired brightness can be secured in a body cavity with the illumination lights emitted from the needle lights 400 even if the endoscope 100 does not include illumination means for illuminating the inside of the body cavity. Accordingly, it is possible to observe a state in the body cavity with the monitor 112.

In addition, since the endoscope 100 does not include illumination means for illuminating the inside of the body cavity, an occupied space for arranging an illumination window and a light guide, which are provided in a conventional endoscope, becomes unnecessary. As a result, an outer diameter of the endoscope insertion part 102 can be reduced, and thus an outer diameter of the outer tube 300 also can be reduced. Therefore, since an opening size of an opening (insertion hole) formed in a body wall can be reduced, it is possible to make a postoperative scar inconspicuous to enable a burden to a testee to be reduced.

In the present embodiment, although there is explained about a case of application to an endoscope without illumination means. However, the present embodiment is not limited to this case. The present embodiment can be applied to an endoscope including auxiliary illumination means capable of emitting auxiliary illumination light, for example. If an endoscope includes the auxiliary illumination means, it is possible to reduce a diameter of the endoscope as compared with a conventional general endoscope, and the same effect as that of the present embodiment can be obtained.

In addition, in the present embodiment, although there is described a case where the needle lights 400 are inserted into a body cavity through the outer tube 500, for an example, there may be an aspect in which needle lights 400 are inserted into a body cavity of a patient without using the outer tube 500.

As above, although the endoscopic surgery device according to the present invention has been described in detail, the present invention is not limited to the examples above, and may include various modifications and variations within a range without departing from the essence of the present invention as a matter of course.

What is claimed is:

1. An endoscopic surgery device comprising:
   a guide member configured to penetrate through a body wall to be inserted into a body cavity, comprising an endoscope insertion path and a treatment tool insertion path within the same guide member, wherein
   the endoscope insertion path which is provided inside the guide member, and into which an endoscope configured to observe an inside of the body cavity is inserted in a back-and-forth movable manner,
   the treatment tool insertion path which is provided inside the same guide member, and into which a treatment tool configured to inspect or treat a diseased part in the body cavity is inserted in a back-and-forth movable manner;
   a position sensor configured to detect a first state where a change of relative position of the treatment tool with respect to the endoscope is not detected and a second state where the change of the relative position of the treatment tool with respect to the endoscope is detected, and configured to detect a movement amount of the treatment tool with respect to the guide member in the second state;
   a processor configured to change a size of an observation target of an observation image acquired by the endoscope in accordance with the movement amount of the treatment tool detected by the position sensor,
   a slider provided in the guide member, and having a first stopper portion and a second stopper portion which are provided separately from each other in a longitudinal direction of the guide member; and
   a sleeve provided in the guide member, and slidably located on a first path formed between the first stopper portion and the second stopper portion,
   wherein the sleeve has a holding hole configured to hold the treatment tool, and
   wherein the position sensor detects the movement amount of the slider.

2. The endoscopic surgery device according to claim 1, wherein
   the treatment tool is provided, on an outer circumference part thereof, with a scale area corresponding to the second state which is periodically arranged along an axial direction of the treatment tool, and a non-scale area corresponding to the first state that is arranged other than the scale area, and
   when the treatment tool moves back and forth, the position sensor detects the movement amount of the treatment tool by optically, magnetically, or electronically reading the scale area, and does not detect the movement amount of the treatment tool in the non-scale area.

3. The endoscopic surgery device according to claim 1, wherein the position sensor includes:
   a calculation unit configured to calculate the movement amount of the treatment tool in the observation image;
   a first conversion unit configured to convert the movement amount of the treatment tool in the observation image calculated by the calculation unit into an actual movement amount; and
   a second conversion unit configured to set the actual movement amount of the treatment tool to zero when the actual movement amount of the treatment tool is less than a predetermined range.

4. The endoscopic surgery device according to claim 1, wherein the processor changes the size of the observation target of the observation image acquired by the endoscope in proportion to the movement amount of the treatment tool.

5. The endoscopic surgery device according to claim 1, further comprising an endoscope driver which comprises a motor and a gear, connected to the endoscope and configured to move the endoscope along the endoscope insertion path,
   wherein the processor is configured to control back and forth movement of the endoscope inserted into the endoscope insertion path by the endoscope driver based on a detection result of the position sensor.

6. The endoscopic surgery device according to claim 1, further comprising a processor control unit connected to the endoscope and configured to control the endoscope,
   wherein the processor control unit is configured to change magnification of the observation image acquired by the endoscope based on a detection result of the position sensor.

7. The endoscopic surgery device according to claim 6, wherein
   the endoscope includes a zoom lens configured to be movable in an optical axis direction, and
   the processor control unit includes an optical zoom control unit configured to change the magnification of the observation image by moving the zoom lens in the optical axis direction based on the detection result by the position sensor.

8. The endoscopic surgery device according to claim 6, wherein the processor control unit includes an electronic zoom control unit configured to change the magnification of the observation image acquired by the endoscope, by performing electronic variable magnification processing to the observation image based on the detection result by the position sensor.

9. An endoscopic surgery device comprising:
   a guide member configured to penetrate through a body wall to be inserted into a body cavity, comprising an endoscope insertion path and a treatment tool insertion path within the same guide member, wherein
   the endoscope insertion path which is provided inside the guide member, and into which an endoscope configured to observe an inside of the body cavity is inserted in a back-and-forth movable manner, the treatment tool insertion path which is provided inside the same guide member, and into which a treatment tool configured to inspect or treat a diseased part in the body cavity is inserted in a back-and-forth movable manner;

a position sensor configured to detect a first state where a change of relative position of the treatment tool with respect to the endoscope is not detected and a second state where the change of the relative position of the treatment tool with respect to the endoscope is detected, and configured to detect a movement amount of the treatment tool with respect to the guide member in the second state;

a processor configured to change a size of an observation target of an observation image acquired by the endoscope in accordance with the movement amount of the treatment tool detected by the position sensor;

a processor control unit connected to the endoscope and configured to control the endoscope;

a slider provided in the guide member, and having a first stopper portion and a second stopper portion which are provided separately from each other in a longitudinal direction of the guide member; and a sleeve provided in the guide member, and slidably located on a first path formed between the first stopper portion and the second stopper portion, wherein the processor control unit is configured to change magnification of the observation image acquired by the endoscope based on a detection result of the position sensor;

wherein the sleeve has a first holding hole configured to hold the treatment tool, and wherein the position sensor detects the movement amount of the slider.

10. The endoscopic surgery device according to claim 9, wherein the endoscope includes a zoom lens configured to be movable in an optical axis direction, and the processor control unit includes an optical zoom control unit configured to change the magnification of the observation image by moving the zoom lens in the optical axis direction based on the detection result by the position sensor.

11. The endoscopic surgery device according to claim 9, wherein the processor control unit includes an electronic zoom control unit configured to change the magnification of the observation image acquired by the endoscope, by performing electronic variable magnification processing to the observation image based on the detection result by the position sensor.

12. The endoscopic surgery device according to claim 9, further comprising an endoscope driver, comprising a motor and a gear, connected to the endoscope and configured to move the endoscope along the endoscope insertion path, wherein the processor is configured to control back and forth movement of the endoscope inserted into the endoscope insertion path by the endoscope driver based on a detection result of the position sensor.

\* \* \* \* \*